United States Patent
Gao et al.

(10) Patent No.: US 11,447,474 B2
(45) Date of Patent: Sep. 20, 2022

(54) SOLID FORMS OF A GLYT1 INHIBITOR

(71) Applicant: Boehringer Ingelheim International GmbH, Ingelheim am Rhein (DE)

(72) Inventors: Joe Ju Gao, Southbury, CT (US); Peter Sieger, Mittelbiberach (DE); Bing-Shiou Yang, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 82 days.

(21) Appl. No.: 16/862,608

(22) Filed: Apr. 30, 2020

(65) Prior Publication Data
US 2020/0347041 A1 Nov. 5, 2020

Related U.S. Application Data

(60) Provisional application No. 62/841,401, filed on May 1, 2019.

(51) Int. Cl.
C07D 413/04 (2006.01)

(52) U.S. Cl.
CPC .................. C07D 413/04 (2013.01)

(58) Field of Classification Search
CPC .................................................... C07D 413/04
See application file for complete search history.

(56) References Cited

FOREIGN PATENT DOCUMENTS

WO 2013017657 A1 2/2013

OTHER PUBLICATIONS

Costa et al. Behav. Neurol., 2014, pp. 1-11.*
Armer, Advances in potential therapetic uses of inhitors of CNS selective amino acid transporters, Expert Opinion on Therapeutic Patents, 2001.
Bergeron, Modulation of N-methyl-D-asparate receptor function by glycine transport, Proc. Natl. Sci, vol. 95, 1998.
Boulay, Characterization of SSR103800, a selective inhibitor of the glycine trasporter-1 in models predictive of therapeutic activity in schizophrenia, Pharmacology, Biochem, and Behavior, 2008.
Carlsson, Hypothesis: Is infantile sutism a hypoglutamatergic disorder? Journal of Neural Transmission, 1998.
Cubelos, Localization of the GlyT1 Glycine Transporter, Cerebral Cortex, vol. 15, 2005.
DePoor, Neurochemical, Electrophysiological, and Pharmacological Profiles of the selective Inhibitor of the Glycine Transporter 1, Neuropsychopharmacology, vol. 30, 2005.
Javitt, Treatment of Negative and Cognitive Symptoms, Current Psychiatry Reports, 1999.
Jentsch, The neuropsychopharmacology of Phencyclidine, Neuropsychopharmacology, vol. 20, 1999.
Johnson, Glycine potentiates the NMDA response in cultured mouse brain neurons, Nature, vol. 325, 1987.
Karasawa, d-Serine and a glycine transporter inhibitor improve MK-801-induced cognitive deficits in a novel object recognition test in rats, Behavioural Brain Research, 2007.
Kinney, The glycine Transporter Type 1 Inhibitor N-[3-(4'-Fluorophenyl)-3-4'Phenylphenoxy)Phenylphenoxy)Propyl] Sarcosine Potentiates NMDA Receptor-Mediated Responses in Vivo and Produces an Antipsychotic Profile in Rodent Behavior, The Journal od Neuroscience, 2003.
Lane, Sarcosine (N-Methylglycine) Treatment for Acute Schizophrenia, SOPB, 2008.
Lewis, Catching up on Schizophrenia, Neuron, vol. 28, 2000.
Pralong, Cellular perspectives on glutamate-monomine interactions in limbic lobe structures, Progress in Neurobiology, 2002.
Shimazaki, d-serine and a glycine transporter-1 inhibitor enhance social memory in rats, Psychopharmacology, vol. 209, 2010.
Tsai, Sarcosine (N-Methylglycine) Treatment for Acute Schizophrenia, Biol. Psychiatry, 2008.
Javitt, Translating Glutamate, Neuroscience, 2011.
Zafra, Glycine Transporters are Differentially Expressed among CNS cells, The J. of Neuroscience, 1995.

\* cited by examiner

*Primary Examiner* — Samira J Jean-Louis
(74) *Attorney, Agent, or Firm* — David L. Kershner

(57) ABSTRACT

Disclosed are solid forms of an inhibitor of glycine transporter-1 (GlyT1). The invention also relates to methods of making these solid forms, pharmaceutical compositions comprising these solid forms, and their use for medical conditions responsive to treatment with an inhibitor of glycine transporter-1.

4 Claims, 16 Drawing Sheets

SOLID FORMS OF A GLYT1 INHIBITOR

FIELD OF THE INVENTION

The present inventions relate to solid forms of an inhibitor of glycine transporter-1 (GlyT1). The invention also relates to methods of making these solid forms, pharmaceutical compositions comprising these solid forms, and their use for medical conditions responsive to treatment with an inhibitor of glycine transporter-1.

BACKGROUND

Schizophrenia is a progressive and devastating psychiatric disease characterized by episodic positive symptoms such as delusions, hallucinations, thought disorders and psychosis and persistent negative symptoms such as flattened affect, impaired attention, social withdrawal, and cognitive impairments (Lewis D A and Lieberman J A, 2000, Neuron, 28: 325-33).

A hypothesis of schizophrenia was proposed in the mid-1960s based upon the psychotomimetic action caused by the blockade of the glutamate system by compounds like phencyclidine (PCP) and related agents (e.g. ketamine) which are non-competitive antagonists of the glutamate N-methyl-D-aspartate (NMDA) receptor. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45:668-679); see also Jentsch and Roth, 1999, Neuropsychopharmacology 20:201-225). Therefore, increasing NMDA-receptor neurotransmission in the central nervous system offers an opportunity for the development of novel treatment approaches for schizophrenia and also other neurological and psychiatric diseases related to NMDA-receptor and/or glutamatergic dysfunction. The NMDA-receptor is a ligand-gated ion channel composed of a combination of two NR1 and two NR2 subunits and requires the concomitant binding of glutamate at the NR2 subunit and glycine as a co-agonist at the NR1 subunit to be activated (Johnson and Ascher, 1987, Nature 325:529-531). One strategy to enhance NMDA receptor activity is to elevate the glycine concentration in the local microenvironment of synaptic NMDA receptors by inhibition of GlyT1 (Bergeron R. et al., 1998, Proc. Natl. Acad. Sci. USA 95:15730-15734). In fact, clinical studies with direct glycine site agonists D-serine and a prototype GlyT1-inhibitor, sarcosine, which increases glycine in the synaptic cleft, have demonstrated some efficacy for the treatment of negative symptoms and to a lesser extent, positive and cognitive symptoms of schizophrenia (Tsai et al., 2004, Biol. Psychiatry 44:1081-1089; Lane et al., 2005, Biol. Psychiatry 63:9-12).

Recently, clinical efficacy regarding negative symptoms in schizophrenia patients was reported for the GlyT1-inhibitor RG1678 tested in a clinical phase II trial as adjunctive treatment to marketed antipsychotics (Umbricht et al., 2011, Schizophr. Bull. 37(Suppl.1):324).

Efficacy in various animal models/tests for positive and negative symptoms of schizophrenia as well as in several memory tasks have been reported in the literature for different GlyT1-inhibitors. (Depoortere et al., 2005, Neuropsychopharmacology 30:1963-1985; Boulay et al., 2008, Pharmacol. Biochem. Behav. 91:47-58, Karasawa et al., 2008, Behav. Brain Res. 186:78-83; Shimazaki et al., 2010, Psychopharmacology 209:263-270; Kinney et al., 2003, J. Neurosci. 23:7586-7591).

Two distinct glycine transporter genes have been cloned (GlyT1 and GlyT2) from mammalian brain, which give rise to two transporters having 50% amino acid sequence homology. GlyT1 presents four isoforms arising from alternative splicing and alternative promoter usage (Ia, Ib, 1c and Id). Only two of these isoforms have been found in rodent brain (GlyTIa and GlyTIb). GlyT2 also presents some degree of heterogeneity. GlyT1 is known to be located in CNS and in some peripheral tissues, whereas GlyT2 is specific to the CNS, primarily in the hindbrain and spinal cord (Zafra et al., 1995, J. Neurosci. 15:3952-3969). GlyT1 is expressed in glia and neurons, and it is found to be located at glutamatergic synapses (Cubelos et al., 2005, Cereb. Cortex 15:448-459).

Glycine transporter inhibitors are considered for the treatment of neurological and psychiatric disorders. The majority of disease states implicated are psychoses, schizophrenia (Armer R E and Miller D J, 2001, Exp. Opin. Ther. Patents 11: 563-572), psychotic mood disorders such as severe major depressive disorder, mood disorders associated with psychotic disorders such as acute mania or depression, associated with bipolar disorders and mood disorders, associated with schizophrenia, (Pralong E T et. al., 2002, Prog. Neurobiol., 67:173-202), autistic disorders (Carlsson M L, 1998, J. Neural Trans. 105:525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11:563-572).

Increasing activation of NMDA receptors via GlyT1 inhibition may treat psychosis, schizophrenia (positive, negative and cognitive symptoms), dementia and other diseases in which cognitive processes are impaired, such as attention deficit disorders, Alzheimer's disease, or other neurological and psychiatric disorders.

Inhibition of GlyT1 is of high interest, in particular with respect to cognitive impairment associated with Alzheimer's disease or Schizophrenia.

An inhibitory compound of particular interest is example 50 described in WO2013017657, which has the structure shown below (hereinafter "Compound 1"):

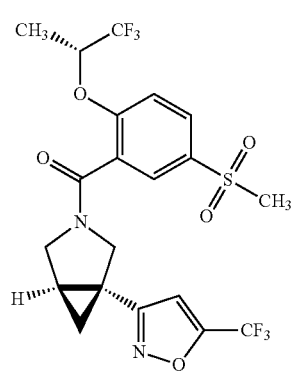

WO2013017657 mentions the structure but does not describe any particular solid form of Compound 1. Thus, there is a need for solid forms of Compound 1 having advantageous pharmaceutical properties such as, for example, processability, stability, and solubility.

BRIEF SUMMARY OF THE INVENTION

The invention relates to novel solid forms of the Compound 1 (herein, collectively "the compounds of the invention").

The invention also relates to methods of making the compounds of the invention and their use as modulators of GlyT1.

In a further aspect, the present invention relates to pharmaceutical compositions, comprising a compound of the invention, optionally together with one or more inert carriers and/or diluents.

A further aspect of the present invention relates to compounds of the invention or pharmaceutical compositions comprising the compounds of the invention for the use in the prevention and/or treatment of neurological or psychiatric disorders.

Yet another aspect of the present invention relates to compounds of the invention or pharmaceutical compositions comprising said compounds for use in the prevention and/or treatment of diseases or conditions which can be influenced by inhibition of GlyT1, such as conditions concerning positive and negative symptoms of schizophrenia as well as cognitive impairments associated with schizophrenia, Alzheimer's Disease and other neurological and psychiatric disorders. The use comprises the manufacture of medicaments for the treatment of the corresponding diseases.

DETAILED DESCRIPTION OF THE INVENTION

Figure 11:
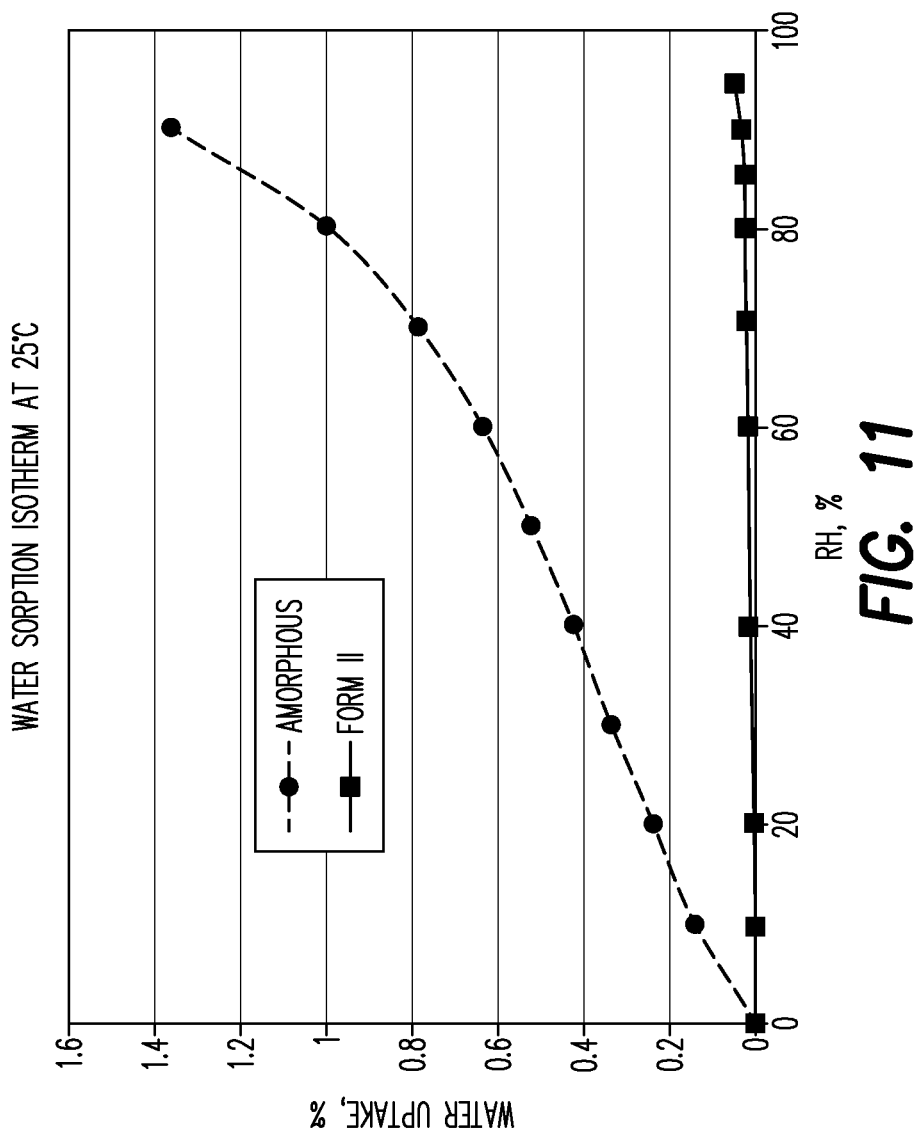
FIG. 11 is a water sorption isotherm showing the water-uptake of Form II of Compound 1 and amorphous Compound 1 when stored at 25° C. at different relative humidities.
Figure 12A:
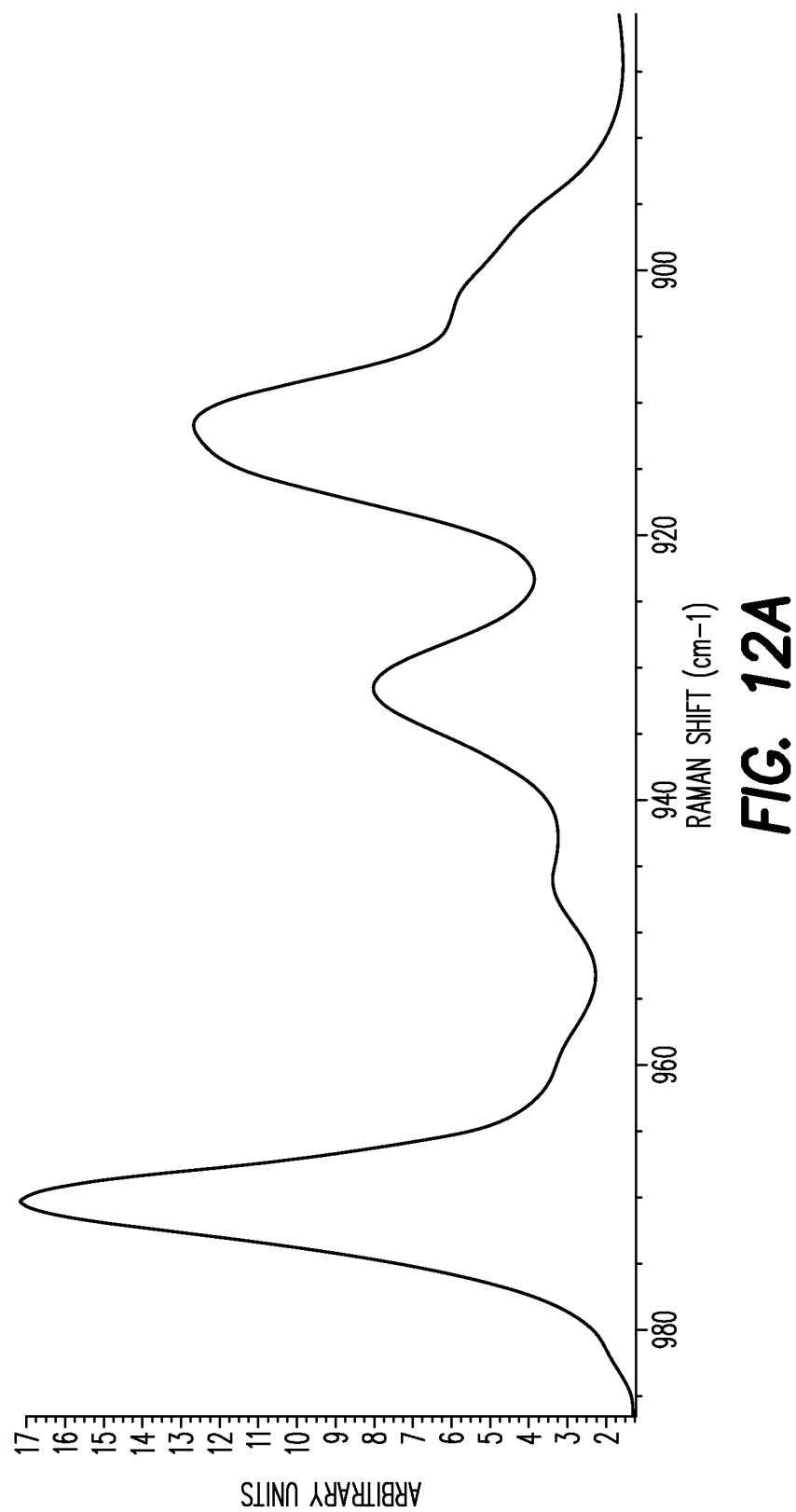
FIG. 12a is a Raman spectrum of Form I of Compound 1.
Figure 12B:
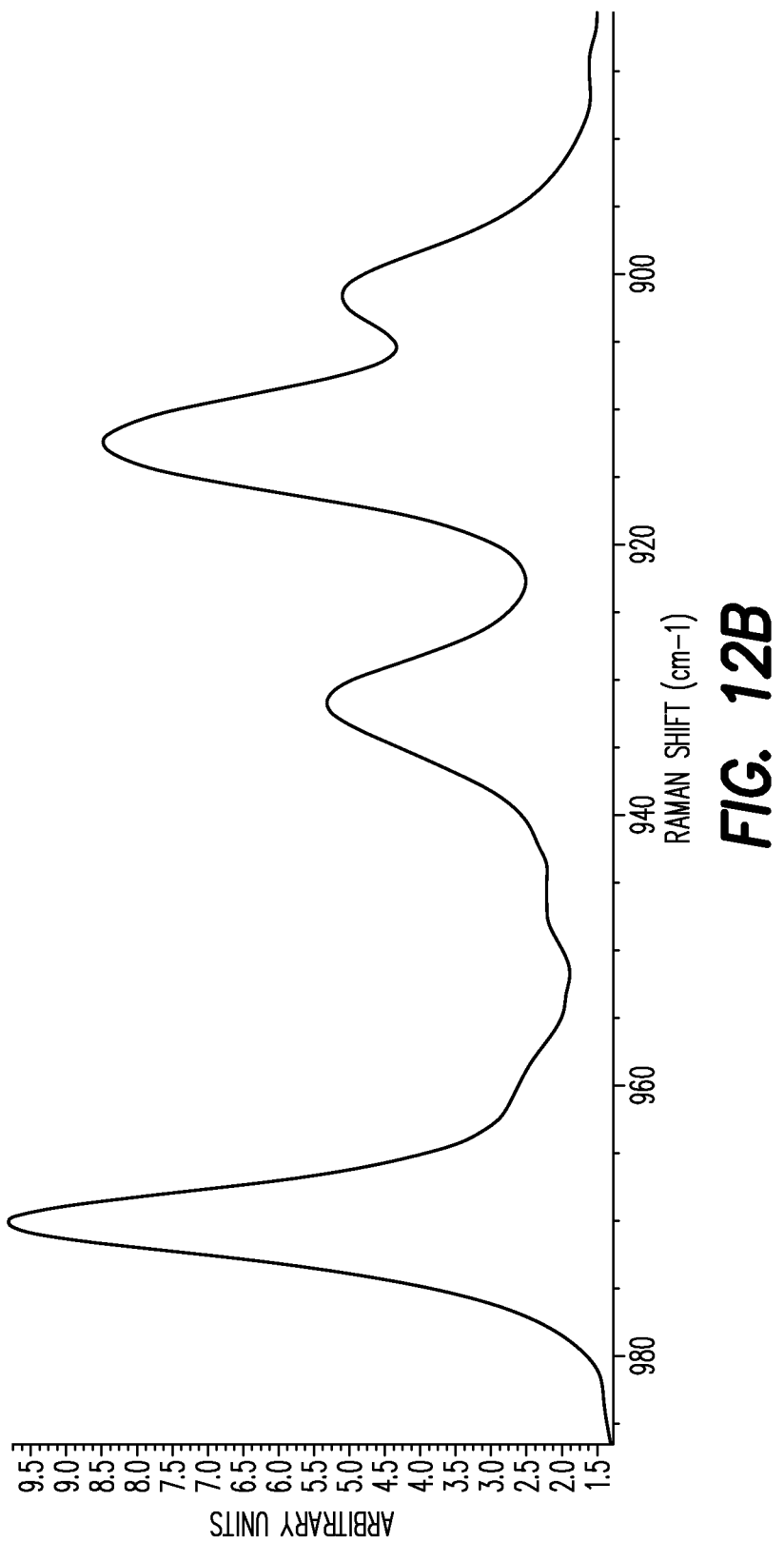
FIG. 12b is a Raman spectrum of Form II of Compound 1.
Figure 12C:
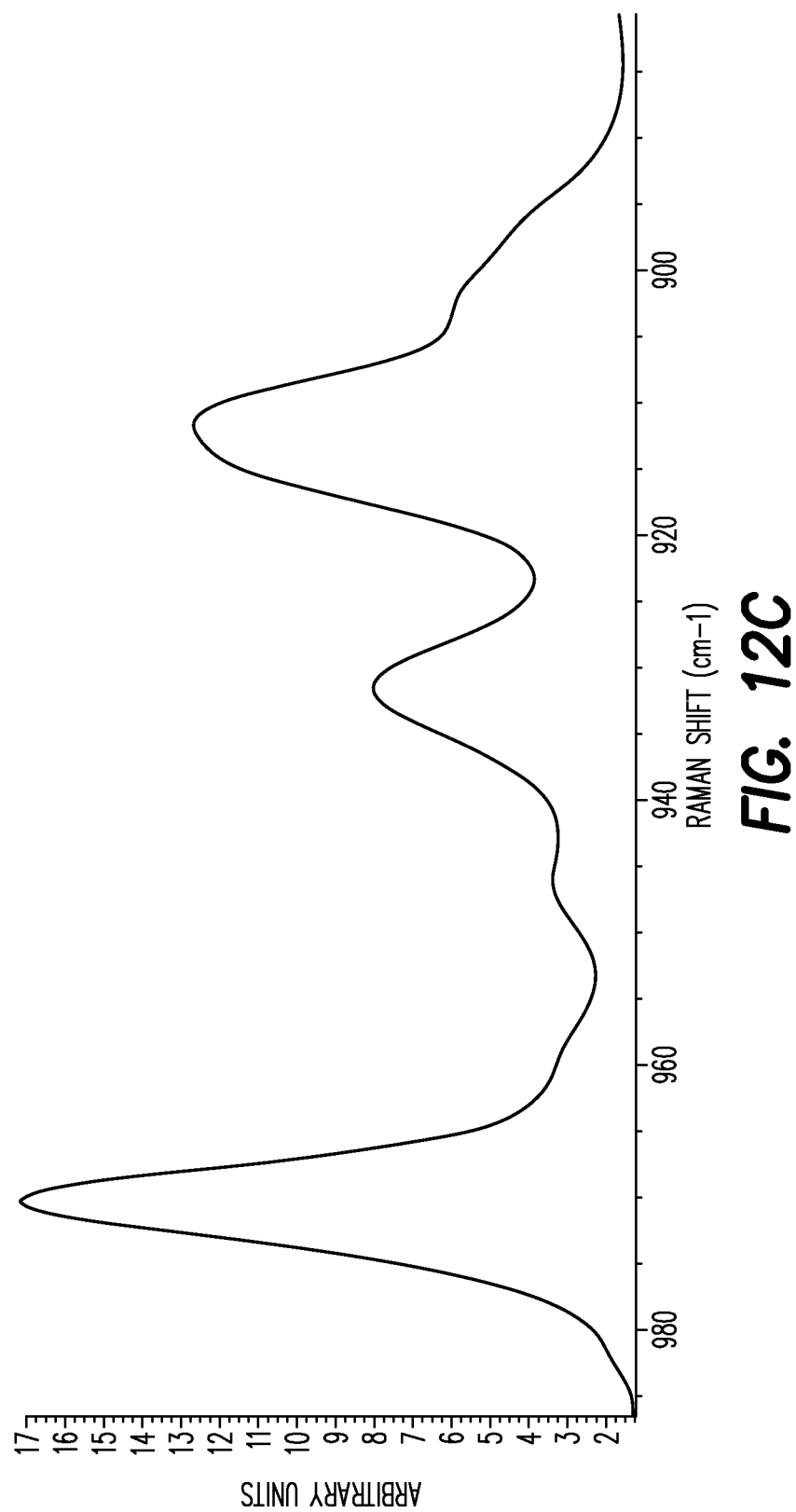
FIG. 12c is a Raman spectrum of Form III of Compound 1.

Abbreviations:
DSC Differential scanning calorimetry
O.D. Outside diameter
RH Relative humidity
SSNMR Solid-state nuclear magnetic resonance
XRPD X-ray powder diffraction As discussed above, the invention relates to crystalline forms of Compound 1 described herein as Form I, Form II, or Form III; and mixtures of at least two of Form I, Form II, or Form III ("the crystalline compounds of the invention"). WO2013017657 makes no mention of any crystalline form of Compound, any method for preparing a crystalline form of Compound 1, or any of the properties of the crystalline forms of Compound 1 described herein. The compounds of the invention have advantageous properties (e.g., improved stability and reproducibility) as compared to the amorphous form of Compound 1 described in Example 1 herein and WO2013017657. Improvements over the amorphous form include, for example, lower hygroscopicity and decreased tendency to convert to a different solid form. For example, the water-uptake of amorphous Compound 1 at 25° C. is 1.4% when maintained at 90% relative humidity for 6 hours under humid nitrogen purge. In contrast, the water-uptake of Form II of Compound 1 (an exemplary compound of the invention) at 25° C. is only about 0.04% when maintained at 90% relative for 6 hours under humid nitrogen purge. (See FIG. 11.)

In one embodiment, the invention relates to the solid Form I of Compound 1.

In one embodiment, the invention relates to the solid Form II of Compound 1.

In one embodiment, the invention relates to the solid Form III of Compound 1.

Each of Form I, Form II and Form III can be prepared in a form that is substantially free of the other two polymorphs. For example, in one embodiment, Form I may be substantially free of Form II and Form III; in another embodiment, Form II may be substantially free of Form I and Form III; and in another embodiment, Form III may be substantially free of Form I and Form II. As used herein, "substantially free" means that the solid compound contains at least about 75% of one crystalline Form of Compound 1 (e.g., Form II) based on total molar amounts of Forms I, Form II, and Form III. The molar ratio of Form I, Form II, or Form III of Compound 1 can be determined, for example, using the methods described herein.

In one embodiment, the crystalline compound of the invention comprises at least 75% of Form I of Compound 1 based on the total molar amount of Form I, Form II, and Form III of Compound 1. In another embodiment, the crystalline compound of the invention comprises at least 80% of Form I of Compound 1 based on the total molar amount of Form I, Form II, and Form III of Compound 1. In another embodiment, the crystalline compound of the invention comprises at least 90% of Form I of Compound 1 based on the total molar amount of Form I, Form II, and Form III of Compound 1. In another embodiment, the crystalline compound of the invention comprises at least 95% of Form I of Compound 1 based on the total molar amount of Form I, Form II, and Form III of Compound 1.

In another embodiment, the crystalline compound of the invention comprises at least 75% of Form II of Compound 1 based on the total molar amount of Form I, Form II, and Form III of Compound 1. In another embodiment, the crystalline compound of the invention comprises at least 80% of Form II of Compound 1 based on the total molar amount of Form I, Form II, and Form III of Compound 1. In another embodiment, the crystalline compound of the invention comprises at least 90% of Form II of Compound 1 based on the total molar amount of Form I, Form II, and Form III of Compound 1. In another embodiment, the crystalline compound of the invention comprises at least 95% of Form II of Compound 1 based on the total molar amount of Form I, Form II, and Form III of Compound 1.

In another embodiment, the crystalline compound of the invention comprises at least 75% of Form III of Compound 1 based on the total molar amount of Form I, Form II, and Form III of Compound 1. In another embodiment, the crystalline compound of the invention comprises at least 80% of Form III of Compound 1 based on the total molar amount of Form I, Form II, and Form III of Compound 1. In another embodiment, the crystalline compound of the invention comprises at least 90% of Form III of Compound 1 based on the total molar amount of Form I, Form II, and Form III of Compound 1. In another embodiment, the crystalline compound of the invention comprises at least 95% of Form III of Compound 1 based on the total molar amount of Form I, Form II, and Form III of Compound 1.

The invention also relates to Compound 1 comprising at least two of Form I, Form II, or Form III. In one embodiment, the invention relates to Compound 1 comprising a mixture of Form I and Form II; in another embodiment, the invention relates to Compound 1 comprising a mixture of Form I and Form III; in another embodiment, the invention relates to Compound 1 comprising a mixture of Form II and Form III; and in another embodiment, the invention relates to Compound 1 comprising a mixture of Form I, Form II and Form III.

The invention also relates to combinations of amorphous forms of Compound 1 and one or more crystalline forms of Compound 1 described herein as Form I, Form II, or Form III.

Characterization

The compounds of the invention can be characterized by the methods described below. Methods of preparing each of Form I, Form II or Form III are described in the Experimental section.

X-Ray Powder Diffraction (XRPD)

Figure 1:
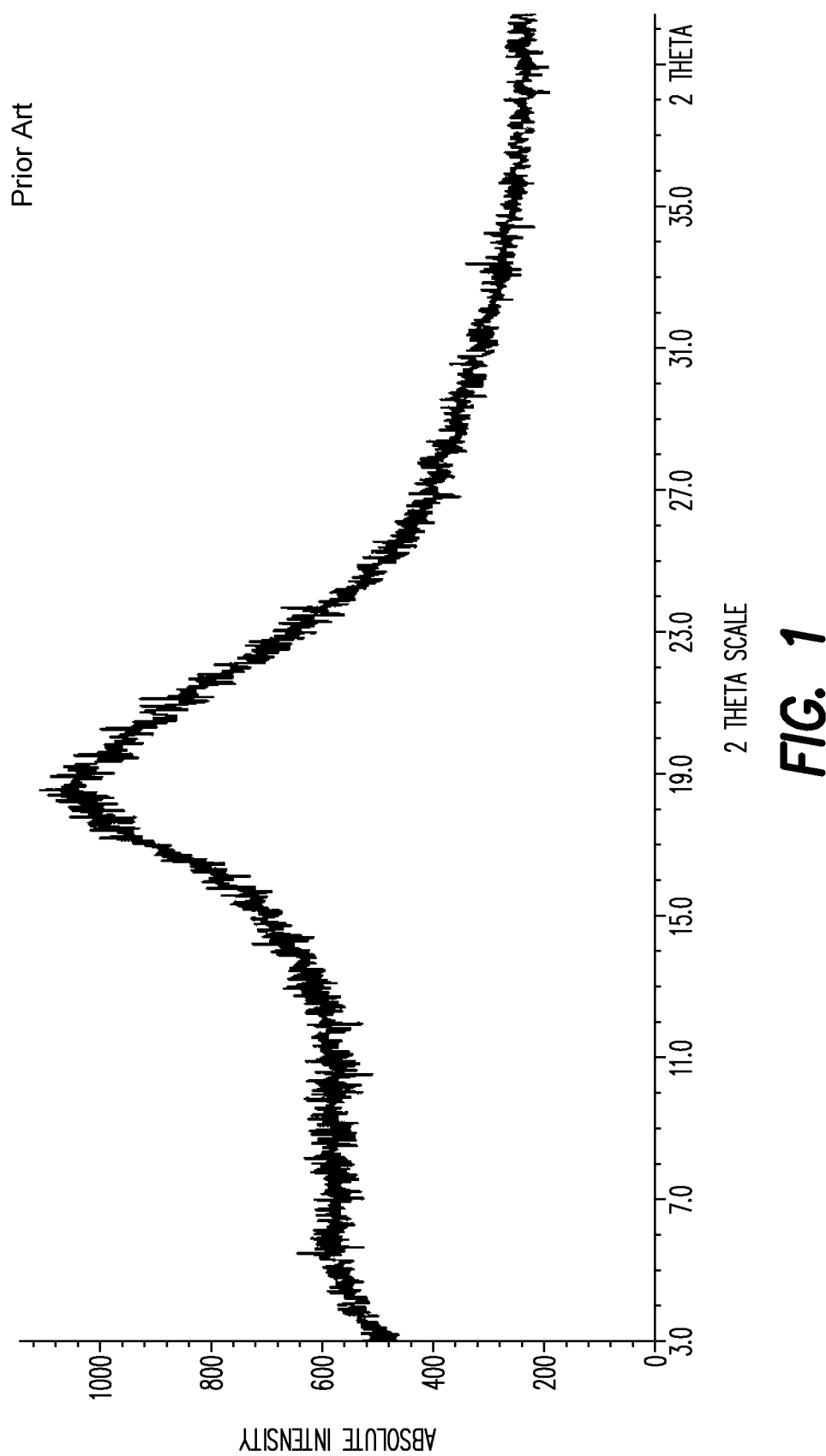
FIG. 1 shows an XRPD pattern of Compound 1 (amorphous form) prepared according to the procedure of WO2013017657.

X-ray powder diffraction analyses for samples of Form I, Form II, and Form III are conducted on a Bruker AXS X-Ray Powder Diffractometer Model D8 Advance, using CuKa radiation (1.54 A) in parafocusing mode with a graphite monochromator and a scintillation detector. Each pattern is obtained by scanning over a range of 2 degrees-35 degrees 2 T, step size of 0.05 degrees 2 T, step time of 4 sec per step. Exemplary XRPD spectra of Form I, Form II, and Form III are found in FIGS. 2, 5 and 8, respectively. An exemplary XRPD spectrum of an amorphous form of Compound 1 is shown in FIG. 1. Tables 1, 3 and 5 include the X-ray powder diffraction (XRPD) characteristics for Forms I, II, and III, respectively. The values reported in Tables 1, 3, and 5 have a standard deviation of ±0.2 2θ.

Differential Scanning Calorimetry (DSC)

DSC analysis is performed with a differential scanning calorimeter (Q2000, TA instruments, New Castle, Del.), using general procedure. About 5 mg of powder was weighed into a crimped aluminum pan with pin hole. The sample is heated at 10° C./min from room temperature to 250° C. using the Q2000 DSC. Exemplary DSC traces of Form I, Form II and Form III are found in FIGS. 3, 6 and 9, respectively. Results are reported below.

Water Sorption

Water sorption isotherms are determined using a dynamic vapor sorption system (Advantage, DVS, London, UK). The samples are subjected to 0 to 90% RH stepwise with a step size of 10% at 25° C. Each sample is equilibrated at each RH step for at least 60 min, and equilibrium is assumed if weight increase is less than 0.1% within one minute, and the maximum duration on each RH is 6 hours. Therefore, each sample is held at a given RH for 1 to 6 hours depending on how fast the equilibrium is reached.

Solid-State NMR (SSNMR)

$^{13}$C Solid-state NMR (SSNMR) data for samples of Form I, Form II, and Form III are acquired on a Bruker Avance III NMR spectrometer (Bruker Biospin, Inc., Billerica, Mass.) at 9.4 T ($^1$H=400.46 MHz, $^{13}$C=100.70 MHz). Samples are packed in 4 mm O.D. zirconia rotors with Kel-F® drive tips. A Bruker model 4BL CP BB WVT probe is used for data acquisition and sample spinning about the magic-angle (54.74 degrees). Sample spectrum acquisition uses a spinning rate of 12 kHz. A standard cross-polarization pulse sequence is used with a ramped Hartman-Hahn match pulse on the proton channel at ambient temperature and pressure. The pulse sequence uses a 3 millisecond contact pulse and a 5 second recycle delay. Two-pulse phase modulated (tppm) decoupling is also employed in the pulse sequence. No exponential line broadening is used prior to Fourier transformation of the free induction decay. Chemical shifts are referenced using the secondary standard of adamantane, with the upfield resonance being set to 29.5 ppm. The magic-angle is set using the $^{79}$Br signal from KBr powder at a spinning rate of 5 kHz. Exemplary $^{13}$C SSNMR spectra of Form I, Form II, and Form III are found in FIGS. 4, 7 and 10, respectively. Tables 2a, 4a and 6 include the chemical shifts obtained from $^{13}$C SSNMR spectra acquired for Forms I, II, and III, respectively. The values reported in Tables 2a, 4a, and 6 have a standard deviation of ±0.2 ppm.

$^{19}$F Solid-state NMR (SSNMR) data for samples of Form I, Form II, and Form II are acquired on a Bruker Avance III NMR spectrometer (Bruker Biospin, Inc., Billerica, Mass.) at 9.4 T ($^1$H=400.46 MHz, $^{19}$F=376.76 MHz). Samples are packed in 3.2 mm O.D. zirconia rotors with Kel-F® drive tips. A Bruker model 3.2BL BB probe is used for data acquisition and sample spinning about the magic-angle (54.74 degrees). Sample spectra are acquired with a spinning rate of 22 kHz. A standard spin echo pulse sequence is used with a 12 second recycle delay. SPINAL-64 1H decoupling is also employed. No exponential line broadening is used prior to Fourier transformation of the free induction decay. Chemical shifts are referenced using the most intense signal from polyvinylidene fluoride (PVDF), with the resonance being set to −91 ppm. The magic-angle is set using the $^{79}$Br signal from KBr powder at a spinning rate of 5 kHz. Exemplary $^{19}$F SSNMR spectra of Form I and Form II are found in FIGS. 4*b* and 7*b*, respectively. Tables 2b and 4b include the chemical shifts obtained from $^{19}$F SSNMR spectra acquired for Forms I and II, respectively. The values reported in Tables 2a and 4b have a standard deviation of ±0.2 ppm.

Raman Spectroscopy

Raman spectra for samples of Form I, Form II and Form III are acquired on a Nicolet 6700 FT-Raman Module AEU0900515 spectrometer. Form II exhibits a Raman scattering peak at 901 1/cm, which is not observed in Forms I and III. The relative intensity of this peak may be used to estimate the relative amount of Form II present in the crystalline forms of Compound 1.

Characteristics of Form I

Figure 2:
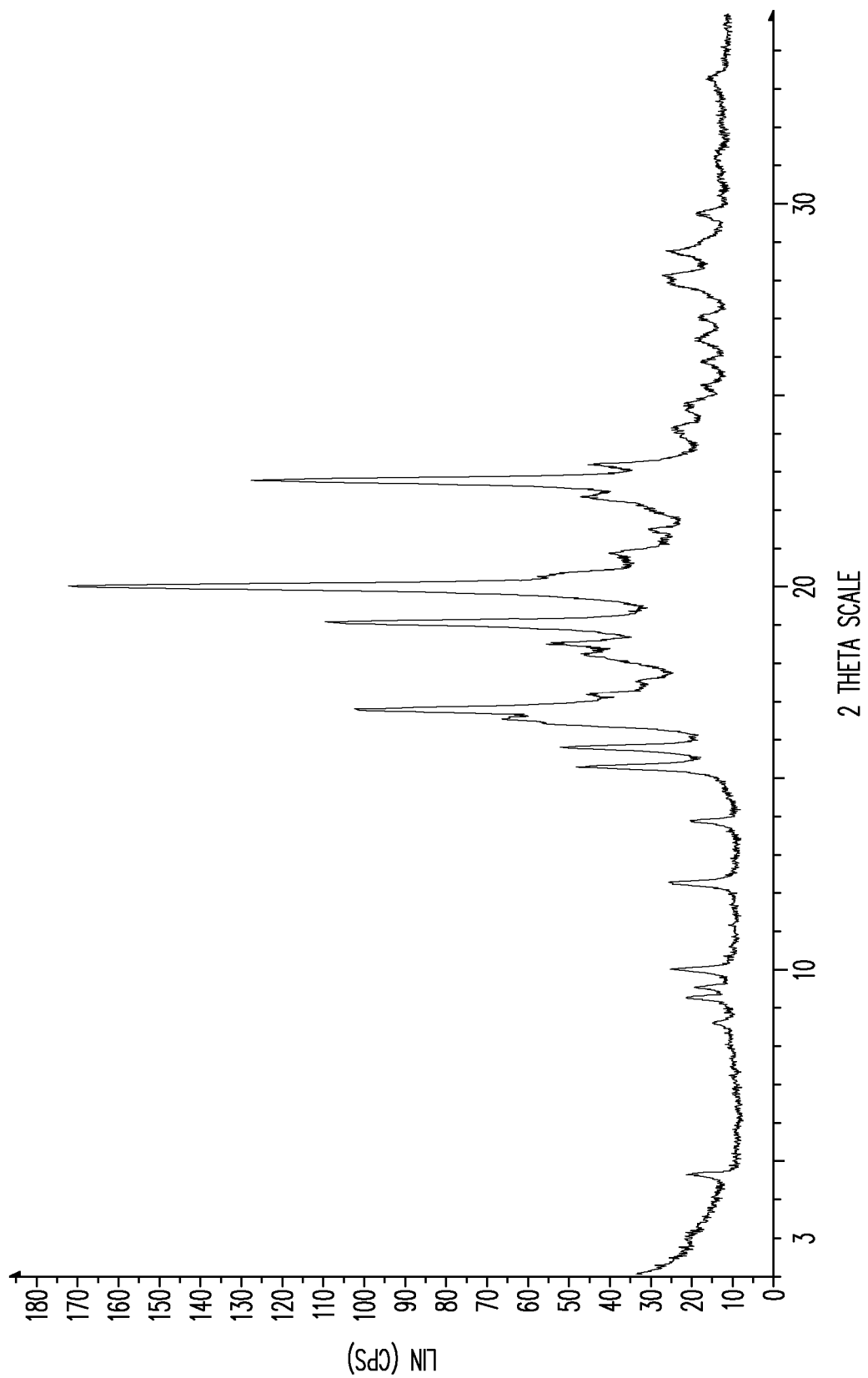
FIG. 2 shows an X-ray powder diffraction (XRPD) pattern of Form I of Compound 1.
Figure 3:
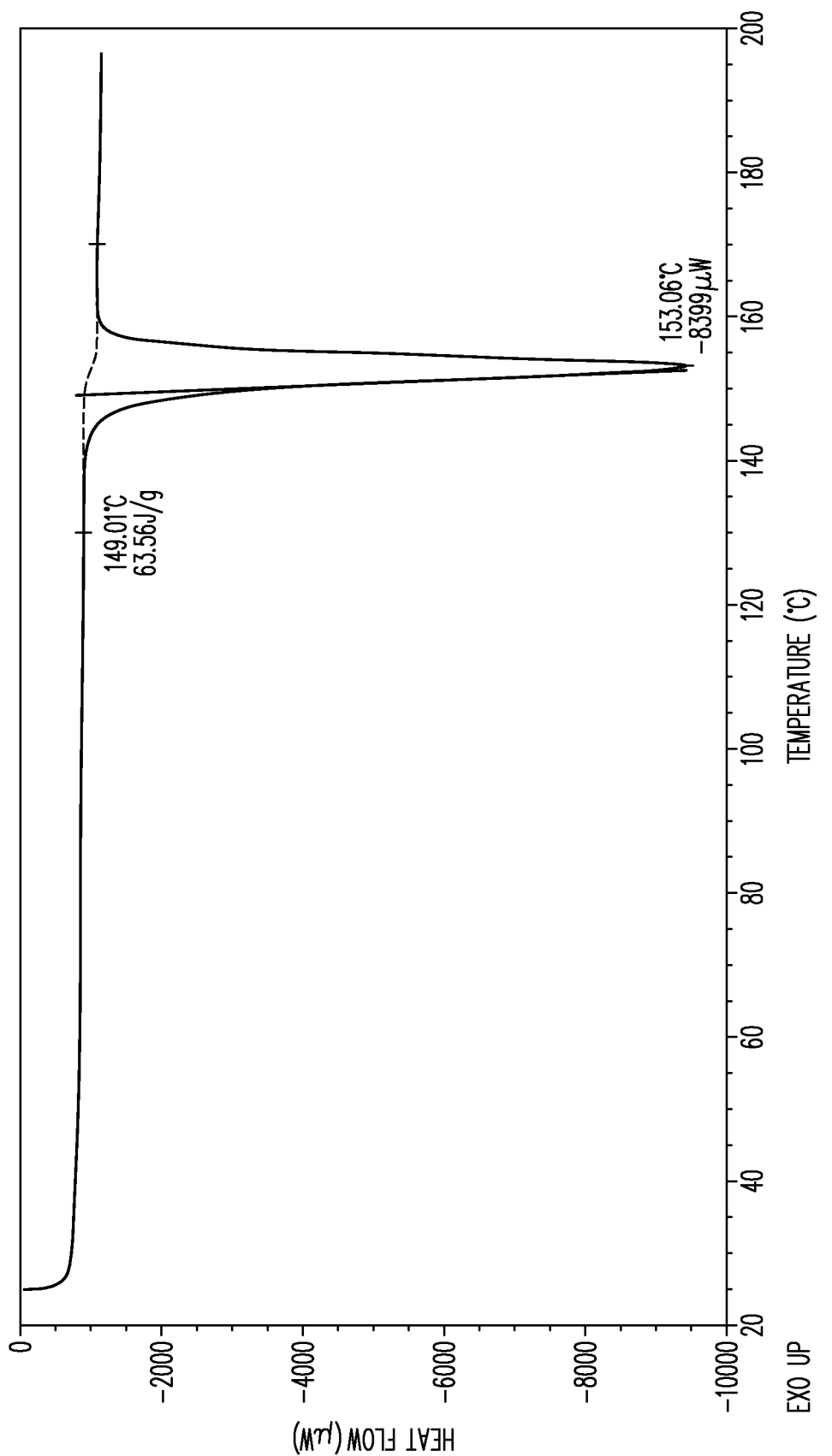
FIG. 3 is a thermal analysis profile of Form I of Compound 1 determined by DSC measurement.
Figure 4A:
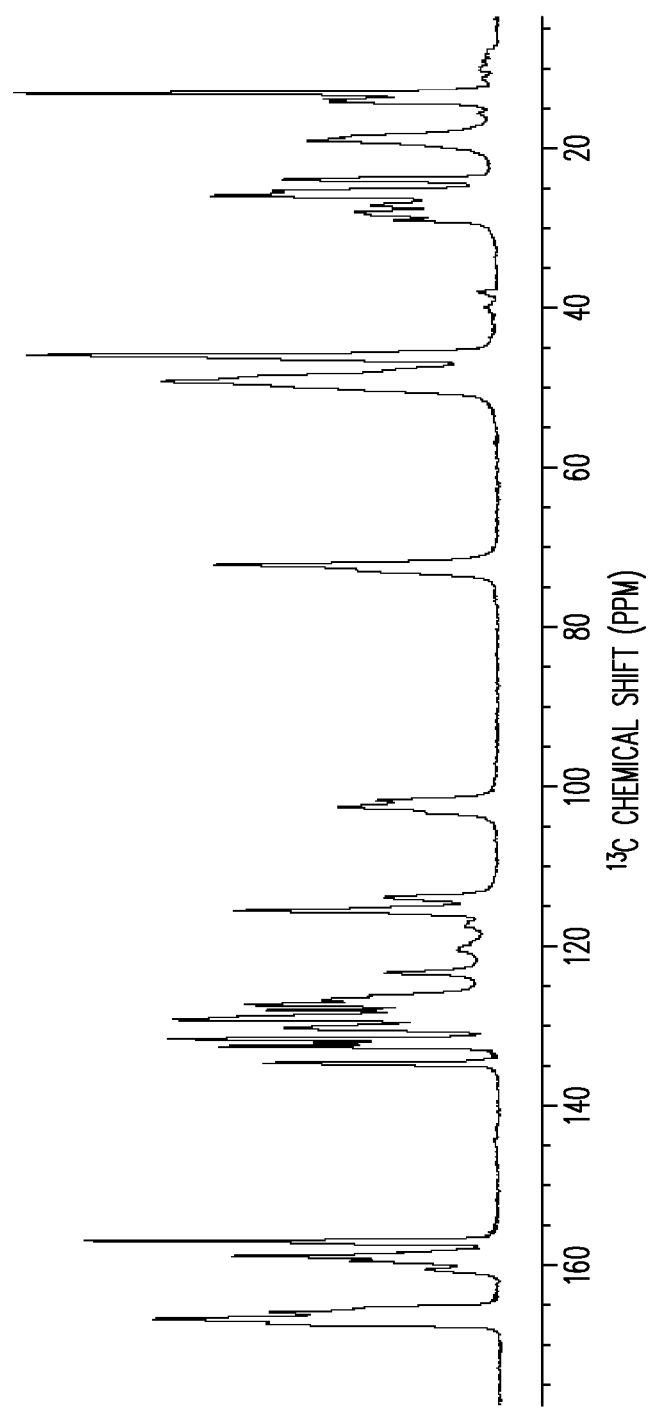
FIG. 4a is a $^{13}$C solid-state NMR spectrum of Form I of Compound 1.
Figure 4B:
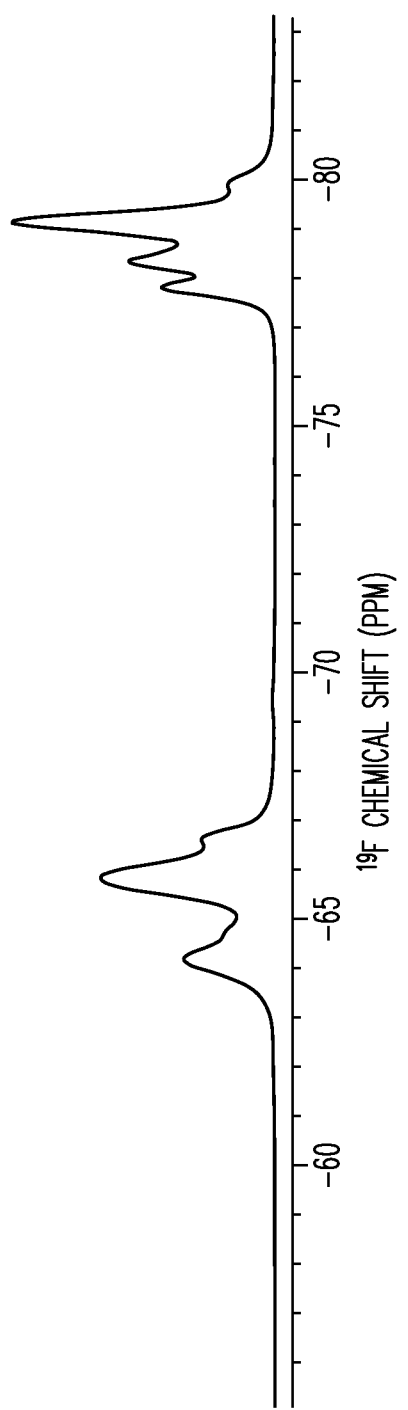
FIG. 4b is a $^{19}$F solid-state NMR spectrum of Form I of Compound 1.

The X-ray powder diffraction (XRPD) pattern of Form I of Compound 1 is shown in FIG. 2; the thermal analysis profile of Form I of Compound 1 determined by DSC measurement is shown in FIG. 3; the $^{13}$C solid state NMR spectrum of Form I of Compound 1 is shown in FIG. 4a; and the $^{19}$F solid state NMR spectrum of Form I of Compound 1 is shown in FIG. 4b.

Characteristic XRPD peaks; $^{13}$C solid-state nuclear magnetic resonance peaks, and $^{19}$F solid-state nuclear magnetic resonance peaks for Form I are provided in Table 1, Table 2a, and Table 2b, respectively.

TABLE 1

X-ray powder diffraction (XRPD) characteristics from FIG. 2 for Form I.

| 2Θ, [°] | Intensity I/I, [%] |
|---|---|
| 4.6 | 5 |
| 7.9 | 1 |
| 8.5 | 4 |
| 9.2 | 6 |
| 9.5 | 6 |
| 10.0 | 11 |
| 12.2 | 12 |
| 13.8 | 6 |
| 15.2 | 6 |
| 15.7 | 6 |
| 16.7 | 40 |
| 17.2 | 11 |
| 17.5 | 5 |
| 18.0 | 3 |
| 18.5 | 8 |
| 19.0 | 59 |
| 20.0 | 100 |
| 20.8 | 4 |
| 21.5 | 6 |
| 22.7 | 80 |
| 23.2 | 12 |
| 24.1 | 2 |
| 24.7 | 2 |
| 25.2 | 1 |
| 25.9 | 4 |
| 26.4 | 2 |
| 27.0 | 2 |
| 27.9 | 6 |
| 28.7 | 6 |
| 29.7 | 4 |
| 33.3 | 2 |

TABLE 2a $^{13}$C NMR Chemical Shifts from FIG. 4a for Form I.

| Peak | Chemical Shift (ppm) |
|---|---|
| 1 | 167.2 |
| 2 | 166.6 |
| 3 | 165.8 |
| 4 | 165.3 |
| 5 | 160.5 |
| 6 | 159.4 |
| 7 | 158.8 |
| 8 | 158.3 |
| 9 | 156.9 |
| 10 | 134.6 |
| 11 | 132.5 |
| 12 | 132.0 |
| 13 | 131.5 |
| 14 | 130.2 |
| 15 | 129.1 |
| 16 | 128.7 |
| 17 | 127.9 |
| 18 | 127.2 |
| 19 | 126.6 |
| 20 | 126.1 |
| 21 | 123.3 |
| 22 | 120.4 |

TABLE 2a-continued $^{13}$C NMR Chemical Shifts from FIG. 4a for Form I.

| Peak | Chemical Shift (ppm) |
|---|---|
| 23 | 119.4 |
| 24 | 117.4 |
| 25 | 115.4 |
| 26 | 113.8 |
| 27 | 102.4 |
| 28 | 101.6 |
| 29 | 72.0 |
| 30 | 49.0 |
| 31 | 46.8 |
| 32 | 45.7 |
| 33 | 28.7 |
| 34 | 27.7 |
| 35 | 26.9 |
| 36 | 25.7 |
| 37 | 25.1 |
| 38 | 23.6 |
| 39 | 18.8 |
| 40 | 18.4 |
| 41 | 14.0 |
| 42 | 13.7 |

TABLE 2b $^{19}$F NMR Chemical Shifts from FIG. 4b for Form I.

| Peak | Chemical Shift (ppm) |
|---|---|
| 1 | −64.3 |
| 2 | −64.8 |
| 3 | −65.9 |
| 4 | −66.8 |
| 5 | −78.0 |
| 6 | −78.5 |
| 7 | −79.3 |
| 8 | −80.0 |

In one embodiment of the invention, Form I of Compound 1 is characterized by the XRPD pattern of FIG. 2.

In another embodiment of the invention, Form I of Compound 1 has the XRPD characteristics shown in Table 1.

In another embodiment of the invention, Form I of Compound 1 is characterized by at least three XRPD peaks at 2Θ angles selected from 4.6°, 10.0°, 16.7° and 18.0°.

In another embodiment of the invention, Form I of Compound 1 is characterized by XRPD peaks at 2Θ angles selected from 4.6°, 10.0°, 16.7°, 19.0°, 20.0° and 22.7°.

In another embodiment of the invention, Form I, of Compound 1 is characterized by XRPD peaks at 2Θ angles selected from 4.6°, 9.2°, 10.0°, 12.2°, 16.7°, 17.2°, 18.5°, 19.0°, 20.0°, and 22.7°. In yet another embodiment of the invention, Form I of Compound 1 is characterized by the $^{13}$C solid-state nuclear magnetic resonance peaks shown in Table 2a. In yet another embodiment of the invention, Form I of Compound 1 is characterized by the $^{19}$F solid-state nuclear magnetic resonance peaks shown in Table 2b.

In another embodiment of the invention, Form I of Compound 1 is characterized by at least three $^{13}$C solid-state nuclear magnetic resonance peaks at chemical shifts selected from 131.5 ppm, 127.2 ppm, 28.7 ppm, and 25.7 ppm.

In another embodiment of the invention, Form I of Compound 1 is characterized by $^{13}$C solid-state nuclear magnetic resonance peaks at chemical shifts selected from 131.5 ppm, 127.2 ppm, 28.7 ppm, and 25.7 ppm.

In another embodiment of the invention, Form I of Compound 1 is characterized by $^{13}$C solid-state nuclear magnetic resonance peaks at chemical shifts selected from 167.2 ppm, 159.4 ppm, 156.9 ppm, 131.5 ppm, 115.4 ppm, 127.2 ppm, 46.8 ppm, 45.7 ppm, 28.7 ppm, 25.7 ppm, and 13.7 ppm.

In another embodiment of the invention, Form I of Compound 1 has the $^{19}$F solid-state nuclear magnetic resonance characteristics shown in Table 2b.

In another embodiment of the invention, Form I of Compound 1 is characterized by at least three $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of Compound 1 is characterized by at least five $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of Compound 1 is characterized $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of Compound 1 has the XRPD characteristics shown in Table 1; or the $^{13}$C solid-state nuclear magnetic resonance peaks shown in Table 2a; or the $^{19}$F solid-state nuclear magnetic resonance peaks shown in Table 2b.

In another embodiment of the invention, Form I of Compound 1 is characterized by at least three XRPD peaks at 2Θ angles selected from 4.6°, 10.0°, 16.7°, and 18.0°; by at least three $^{13}$C solid-state nuclear magnetic resonance peaks at chemical shifts selected from 131.5 ppm, 127.2 ppm, 28.7 ppm, and 25.7 ppm; or by at least three $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of Compound 1 is characterized by XRPD peaks at 2Θ angles selected from 4.6°, 10.0°, 16.7°, and 18.0°; by $^{13}$C solid-state nuclear magnetic resonance peaks at chemical shifts selected from 131.5 ppm, 127.2 ppm, 28.7 ppm, and 25.7 ppm; or by $^{19}$F solid-state nuclear magnetic resonance peaks at chemical shifts selected from −64.3, −64.8, −65.9, −66.8, −78.0, −78.5, −79.3, and −80.0 ppm.

Characteristics of Form II

Figure 5:
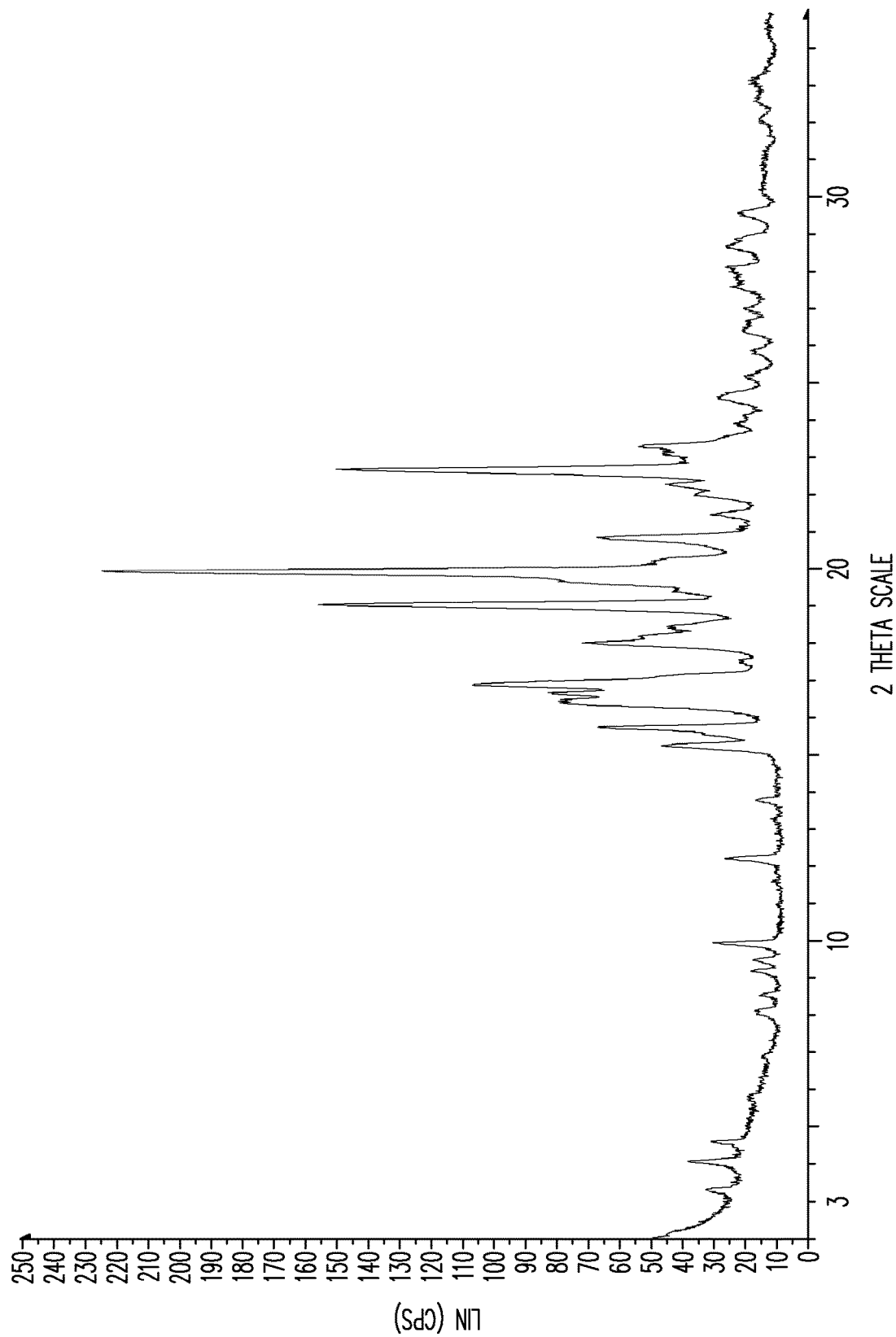
FIG. 5 shows an XRPD pattern of Form II of Compound 1.
Figure 6:
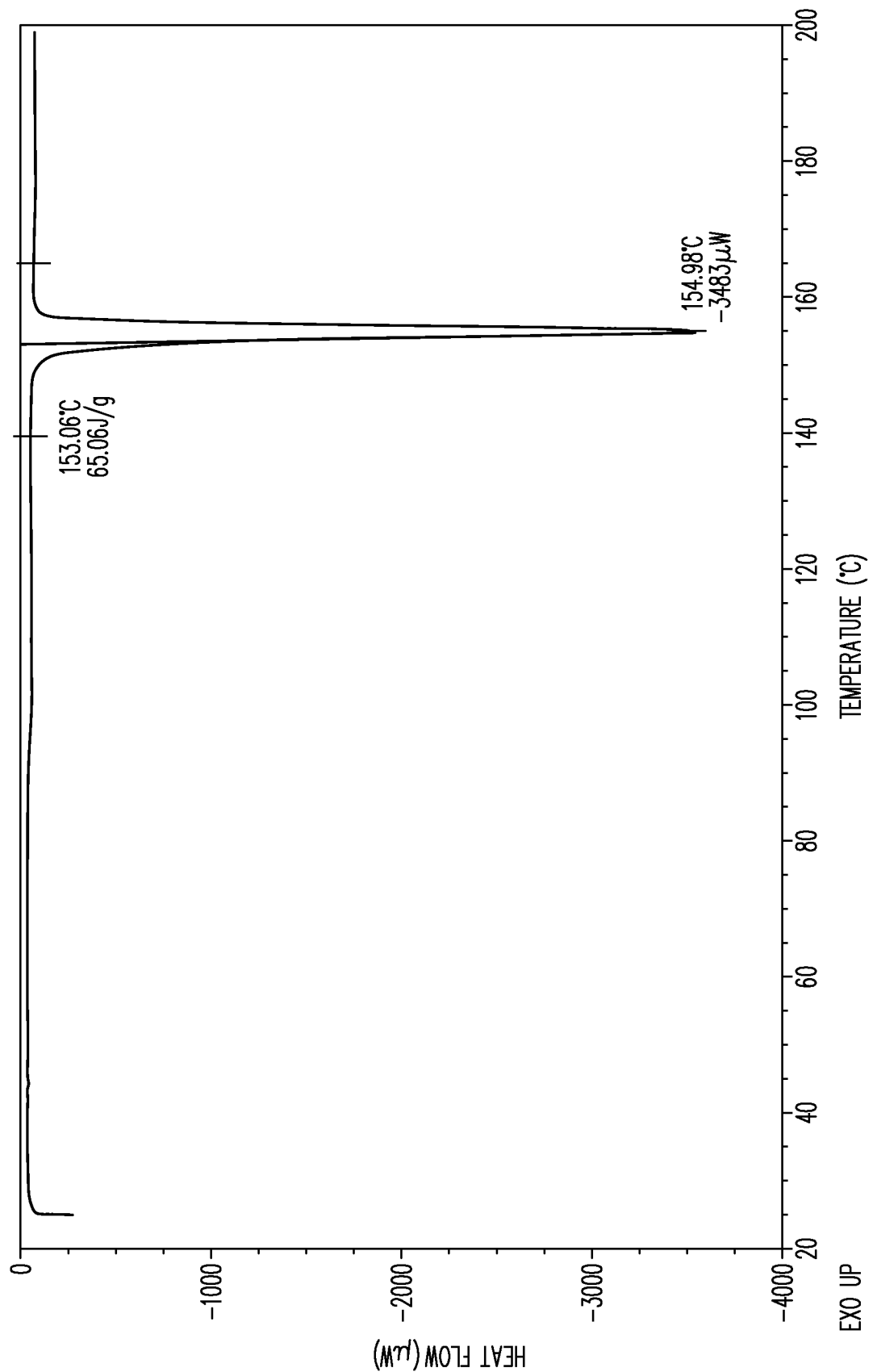
FIG. 6 is a thermal analysis profile of Form II of Compound 1 determined by DSC measurement.
Figure 7A:
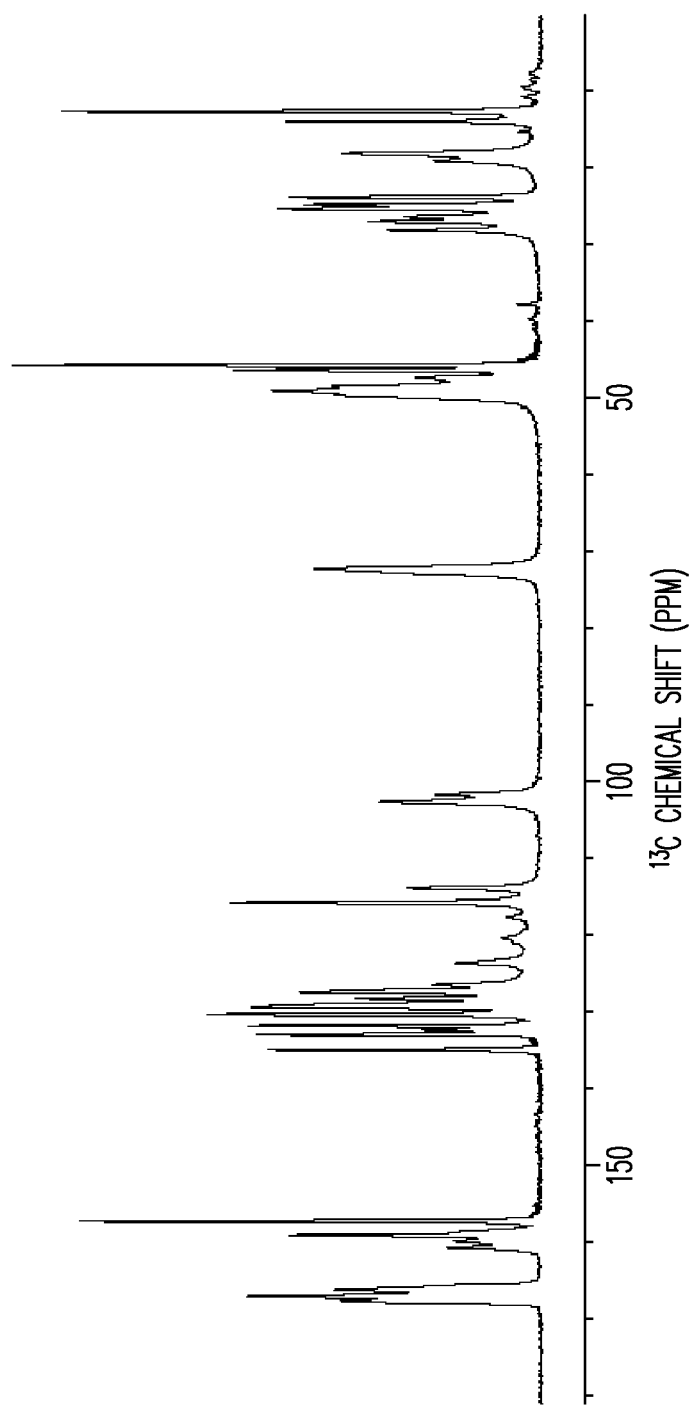
FIG. 7a is a $^{13}$C solid-state NMR spectrum of Form II of Compound 1.
Figure 7B:
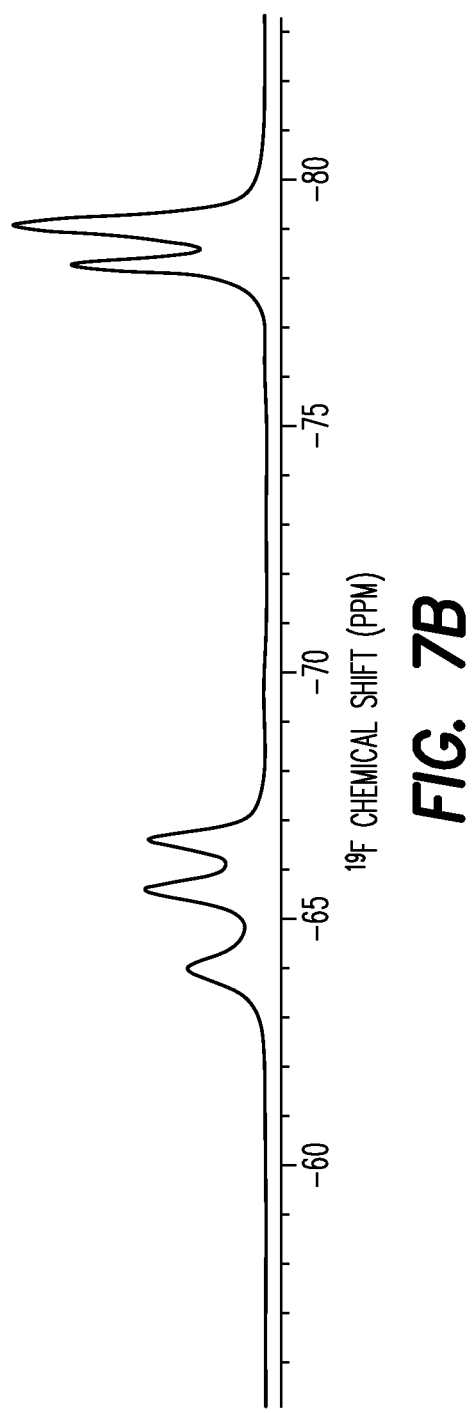
FIG. 7b is a $^{19}$F solid-state NMR spectrum of Form II of Compound 1.

The X-ray powder diffraction (XRPD) pattern of Form II of Compound 1 is shown in FIG. 5; the thermal analysis profile of Form II of Compound 1 determined by DSC measurement is shown in FIG. 6; the $^{13}$C solid-state NMR spectrum of Form II of Compound 1 is shown in FIG. 7a; and the $^{19}$F solid-state NMR spectrum of Form II of Compound 1 is shown in FIG. 7b.

Characteristic XRPD peaks: $^{13}$C solid-state nuclear magnetic resonance peaks, and $^{19}$F solid-state nuclear magnetic resonance peaks for Form II are provided in Table 3, Table 4a, and Table 4b, respectively.

TABLE 3

X-ray powder diffraction (XRPD) characteristics from FIG. 5 for Form II.

| 2Θ, [°] | Intensity I/I, [%] |
|---|---|
| 3.3 | 16 |

TABLE 3-continued

X-ray powder diffraction (XRPD) characteristics from FIG. 5 for Form II.

| 2Θ, [°] | Intensity I/I, [%] |
|---|---|
| 4.1 | 16 |
| 4.6 | 11 |
| 5.8 | 5 |
| 6.9 | 5 |
| 8.1 | 7 |
| 8.6 | 6 |
| 9.2 | 8 |
| 9.5 | 7 |
| 10.0 | 13 |
| 12.2 | 10 |
| 13.8 | 7 |
| 15.3 | 16 |
| 15.8 | 19 |
| 16.7 | 36 |
| 16.9 | 37 |
| 17.6 | 8 |
| 18.0 | 27 |
| 18.5 | 18 |
| 19.1 | 61 |
| 20.0 | 100 |
| 20.9 | 25 |
| 21.5 | 12 |
| 22.7 | 70 |
| 23.3 | 25 |
| 24.0 | 9 |
| 24.7 | 13 |
| 25.2 | 9 |
| 25.9 | 8 |
| 26.5 | 10 |
| 27.1 | 9 |
| 27.9 | 11 |
| 28.8 | 12 |
| 29.6 | 10 |
| 30.2 | 7 |
| 32.2 | 7 |
| 33.2 | 8 |

TABLE 4a $^{13}$C NMR Chemical Shifts from FIG. 7a for Form II.

| Peak | Chemical Shift (ppm) |
|---|---|
| 1 | 167.3 |
| 2 | 166.8 |
| 3 | 165.9 |
| 4 | 160.5 |
| 5 | 159.6 |
| 6 | 158.9 |
| 7 | 157.1 |
| 8 | 134.7 |
| 9 | 132.7 |
| 10 | 132.1 |
| 11 | 131.6 |
| 12 | 130.1 |
| 13 | 129.2 |
| 14 | 128.0 |
| 15 | 127.3 |
| 16 | 126.3 |
| 17 | 123.5 |
| 18 | 120.2 |
| 19 | 117.5 |
| 20 | 115.6 |
| 21 | 113.8 |
| 22 | 102.6 |
| 23 | 101.7 |
| 24 | 72.2 |
| 25 | 49.8 |
| 26 | 49.2 |

TABLE 4a-continued

<sup>13</sup>C NMR Chemical Shifts from FIG. 7a for Form II.

| Peak | Chemical Shift (ppm) |
|---|---|
| 27 | 48.6 |
| 28 | 47.9 |
| 29 | 47.6 |
| 30 | 46.9 |
| 31 | 46.6 |
| 32 | 45.9 |
| 33 | 28.3 |
| 34 | 27.2 |
| 35 | 26.5 |
| 36 | 25.5 |
| 37 | 25.0 |
| 38 | 24.0 |
| 39 | 19.3 |
| 40 | 18.4 |
| 41 | 14.2 |
| 42 | 13.6 |
| 43 | 12.9 |

TABLE 4b

<sup>19</sup>F NMR Chemical Shifts from FIG. 7b for Form II.

| Peak | Chemical Shift (ppm) |
|---|---|
| 1 | −64.0 |
| 2 | −65.6 |
| 3 | −66.6 |
| 4 | −78.2 |
| 5 | −79.1 |

In one embodiment of the invention, Form II of Compound 1 is characterized by the XRPD pattern of FIG. 5.

In another embodiment of the invention, Form II of Compound 1 has the XRPD characteristics shown in Table 3.

In another embodiment of the invention, Form II of Compound 1 is characterized by at least three XRPD peaks at 2Θ angles selected from 4.1°, 4.6°, 10.0°, 16.7°, and 18.0°.

In another embodiment of the invention, Form II of Compound 1 is characterized by at least four XRPD peaks at 2Θ angles selected from 4.1°, 4.6°, 10.0°, 16.7°, and 18.0°.

In another embodiment of the invention, Form II of Compound 1 is characterized XRPD peaks at 2Θ angles selected from 4.1°, 4.6°, 10.0°, 16.7°, and 18.0°.

In another embodiment of the invention, Form II of Compound 1 is characterized XRPD peaks at 2Θ angles selected from 4.1°, 4.6°, 10.0°, 15.8°, 18.0°, 18.5°, 19.1°, 20.0°, 20.9°, 22.7°, and 23.3°.

In yet another embodiment of the invention, Form II of Compound 1 has the $^{13}$C solid-state nuclear magnetic resonance characteristics shown in Table 4a.

In another embodiment of the invention, Form II of Compound 1 is characterized by $^{13}$C solid-state nuclear magnetic resonance peaks at chemical shifts selected from 130.1 ppm, 46.6 ppm, and 25.0 ppm.

In another embodiment of the invention, Form II of Compound 1 is characterized by $^{13}$C solid-state nuclear magnetic resonance peaks at chemical shifts selected from 167.3 ppm, 157.1 ppm, 130.1 ppm, 115.6 ppm, 72.2 ppm, 47.9 ppm, 46.6 ppm, 45.9 ppm, 25.0 ppm, and 12.9 ppm.

In another embodiment of the invention, Form II of Compound 1 has the $^{19}$F solid-state nuclear magnetic resonance characteristics shown in Table 4b.

In another embodiment of the invention, Form II of Compound 1 is characterized by at least three $^{19}$F solid-state nuclear magnetic resonance peaks at chemical shifts selected from −64.0, −65.6, −66.6, −78.2, and −79.1 ppm.

In another embodiment of the invention, Form II of Compound 1 is characterized by $^{19}$F solid-state nuclear magnetic resonance peaks at chemical shifts selected from −64.0, −65.6, −66.6, −78.2, and −79.1 ppm.

In another embodiment of the invention, Form II of Compound 1 has the XRPD characteristics shown in Table 3; or the $^{13}$C solid-state nuclear magnetic resonance peaks shown in Table 4a; or the $^{19}$F solid-state nuclear magnetic resonance peaks shown in Table 4b.

In another embodiment of the invention, Form II of Compound 1 is characterized by at least three XRPD peaks at 2Θ angles selected from 4.1°, 4.6°, 10.0°, 16.7°, and 18.0°; by $^{13}$C solid-state nuclear magnetic resonance peaks at chemical shifts selected from 130.1 ppm, 46.6 ppm, and 25.0 ppm; or by at least three $^{19}$F solid-state nuclear magnetic resonance peaks at chemical shifts selected from −64.0, −65.6, −66.6, −78.2, and −79.1 ppm.

In another embodiment of the invention, Form II of Compound 1 is characterized by at least four XRPD peaks at 2Θ angles selected from 4.1°, 4.6°, 10.0°, 16.7°, and 18.0°; by $^{13}$C solid-state nuclear magnetic resonance peaks at chemical shifts selected from 130.1 ppm, 46.6 ppm, and 25.0 ppm; or by $^{19}$F solid-state nuclear magnetic resonance peaks at chemical shifts selected from −64.0, −65.6, −66.6, −78.2, and −79.1 ppm.

In another embodiment of the invention, Form II of Compound 1 is characterized by XRPD peaks at 2Θ angles selected from 4.1°, 4.6°, 10.0°, 16.7°, and 18.0°; by $^{13}$C solid-state nuclear magnetic resonance peaks at chemical shifts selected from 130.1 ppm, 46.6 ppm, and 25.0 ppm; or by $^{19}$F solid-state nuclear magnetic resonance peaks at chemical shifts selected from −64.0, −65.6, −66.6, −78.2, and −79.1 ppm.

Characteristics of Form III

Figure 8:
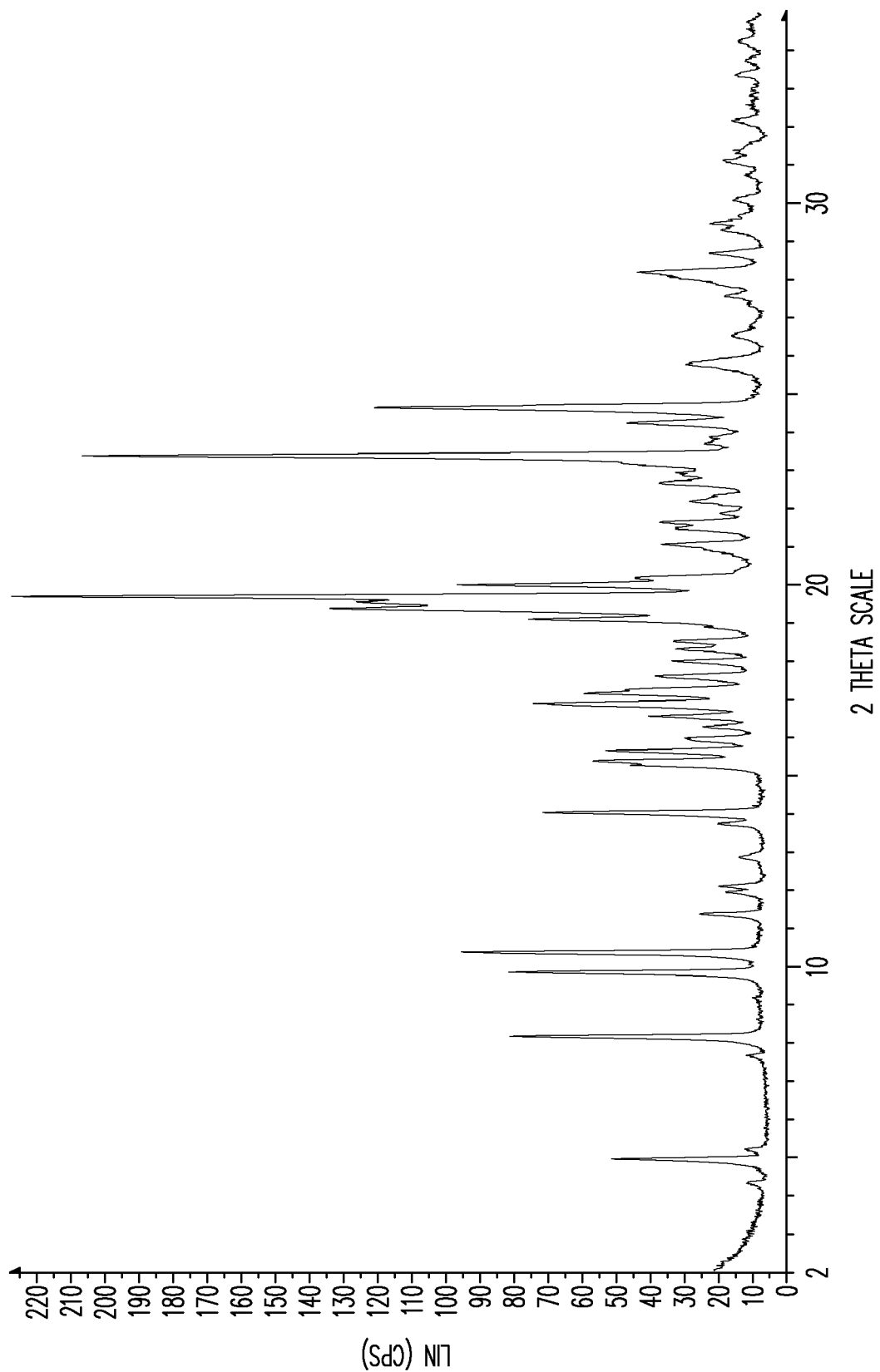
FIG. 8 shows an XRPD pattern of Form III of Compound 1.
Figure 9:
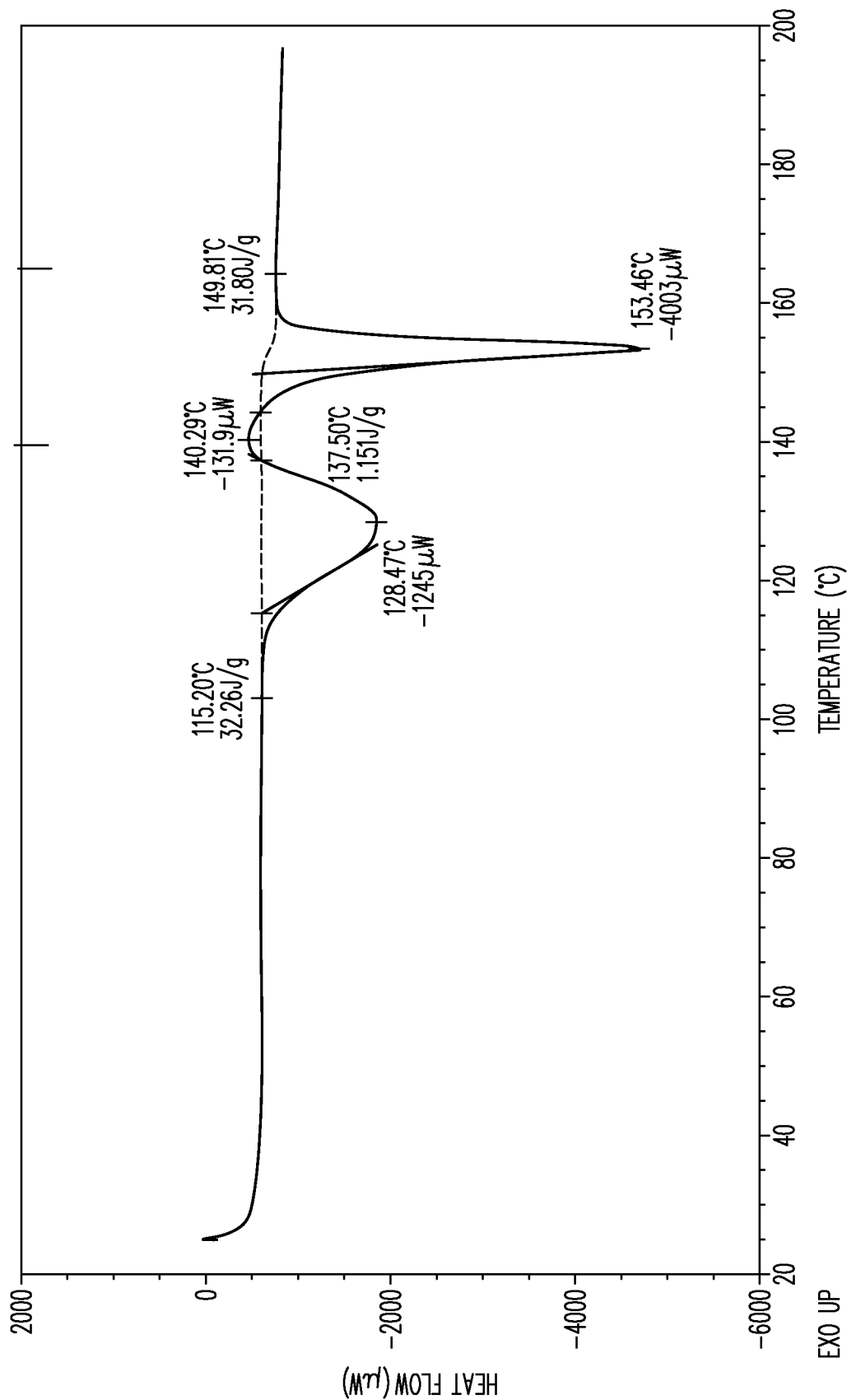
FIG. 9 is a thermal analysis profile of Form III of Compound 1 determined by DSC measurement.
Figure 10:
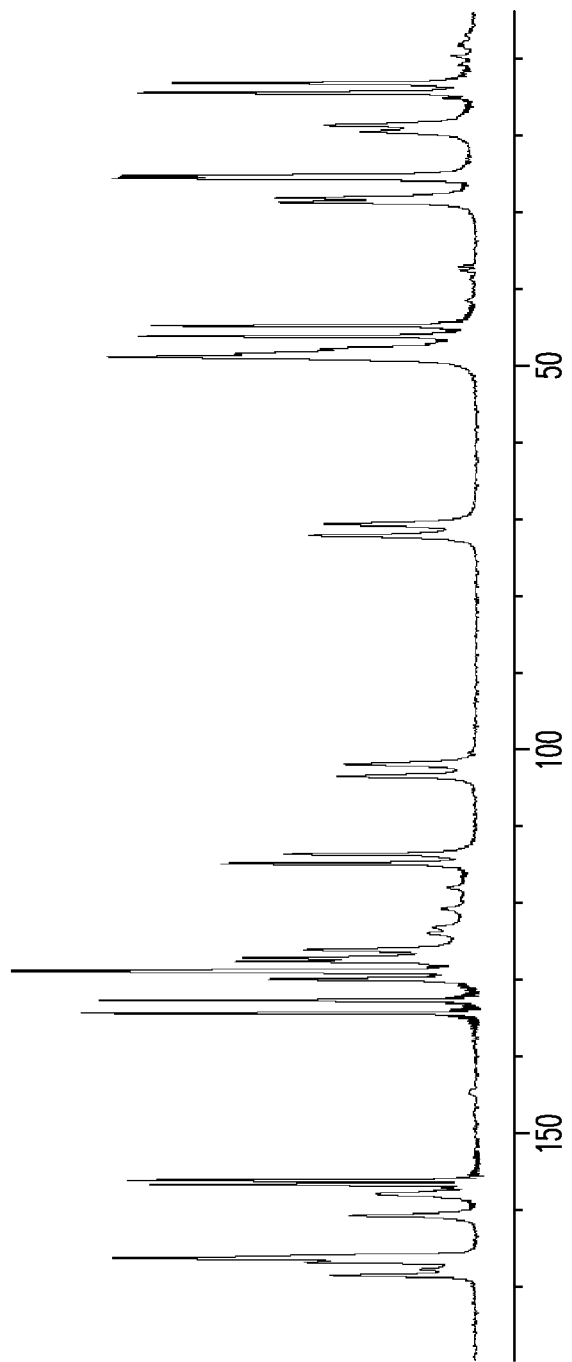
FIG. 10 is a $^{13}$C solid-state NMR spectrum of Form III of Compound 1.

The X-ray powder diffraction (XRPD) pattern of Form III of Compound 1 is shown in FIG. 8; the thermal analysis profile of Form III of Compound 1 determined by DSC measurement is shown in FIG. 9; and the $^{13}$C solid-state NMR spectrum of Form III of Compound 1 is shown in FIG. 10.

Characteristic XRPD peaks and $^{13}$C solid-state nuclear magnetic resonance peaks for Form III are provided in Table 5 and Table 6, respectively.

TABLE 5

X-ray powder diffraction (XRPD) characteristics from FIG. 8 for Form III.

| 2Θ, [°] | Intensity I/I, [%] |
|---|---|
| 4.2 | 5 |
| 4.8 | 22 |
| 5.1 | 5 |
| 7.6 | 4 |
| 8.1 | 28 |
| 9.7 | 38 |
| 10.3 | 37 |
| 11.3 | 10 |
| 11.9 | 6 |
| 12.0 | 8 |

TABLE 5-continued

X-ray powder diffraction (XRPD)
characteristics from FIG. 8 for Form III.

| 2Θ, [°] | Intensity I/I, [%] |
| --- | --- |
| 12.8 | 5 |
| 13.7 | 8 |
| 13.9 | 28 |
| 15.2 | 19 |
| 15.3 | 21 |
| 15.6 | 11 |
| 15.9 | 9 |
| 16.2 | 8 |
| 16.5 | 9 |
| 16.8 | 21 |
| 17.1 | 19 |
| 17.5 | 9 |
| 17.9 | 11 |
| 18.2 | 13 |
| 18.4 | 13 |
| 19.0 | 28 |
| 19.3 | 34 |
| 19.6 | 100 |
| 19.9 | 30 |
| 21.0 | 9 |
| 21.4 | 11 |
| 21.6 | 10 |
| 21.8 | 5 |
| 22.1 | 8 |
| 22.6 | 12 |
| 22.8 | 14 |
| 23.3 | 91 |
| 23.6 | 8 |
| 24.2 | 15 |
| 24.6 | 50 |
| 25.7 | 9 |
| 26.5 | 6 |
| 27.5 | 6 |
| 28.1 | 14 |
| 28.6 | 8 |
| 29.4 | 8 |
| 30.0 | 5 |
| 31.0 | 6 |
| 32.1 | 5 |
| 33.3 | 5 |
| 34.2 | 4 |

TABLE 6

$^{13}$C NMR Chemical Shifts
from FIG. 10 for Form III.

| Peak | Chemical Shift (ppm) |
| --- | --- |
| 1 | 168.4 |
| 2 | 167.6 |
| 3 | 166.6 |
| 4 | 166.1 |
| 5 | 160.5 |
| 6 | 157.8 |
| 7 | 156.6 |
| 8 | 156.0 |
| 9 | 134.2 |
| 10 | 132.5 |
| 11 | 129.8 |
| 12 | 128.7 |
| 13 | 127.4 |
| 14 | 127.0 |
| 15 | 125.9 |
| 16 | 114.7 |
| 17 | 113.5 |
| 18 | 103.4 |
| 19 | 101.8 |
| 20 | 71.9 |
| 21 | 70.5 |
| 22 | 48.7 |
| 23 | 48.3 |
| 24 | 47.6 |
| 25 | 46.0 |
| 26 | 44.6 |
| 27 | 28.5 |
| 28 | 27.9 |
| 29 | 25.5 |
| 30 | 25.1 |
| 31 | 19.4 |
| 32 | 18.5 |
| 33 | 14.3 |
| 34 | 13.0 |

In one embodiment of the invention, Form III of Compound 1 is characterized by the XRPD pattern of FIG. 8.

In another embodiment of the invention, Form III of Compound 1 has the XRPD characteristics shown in Table 5.

In another embodiment of the invention, Form III of Compound 1 is characterized by at least three XRPD peaks at 2Θ angles selected from 4.8°, 9.7°, 10.3°, 13.9°, and 24.6°.

In another embodiment of the invention, Form III of Compound 1 is characterized by at least four XRPD peaks at 2Θ angles selected from 4.8°, 9.7°, 10.3°, 13.9°, and 24.6°.

In another embodiment of the invention, Form III of Compound 1 is characterized by XRPD peaks at 2Θ angles selected from 4.8°, 9.7°, 10.3°, 13.9°, and 24.6°.

In another embodiment of the invention, Form III of Compound 1 is characterized by XRPD peaks at 2Θ angles selected from 4.8°, 8.1°, 9.7°, 10.3°, 13.9°, 19.3°, 19.6°, 23.3°, and 24.6°.

In another embodiment of the invention, Form III of Compound 1 has the $^{13}$C solid-state nuclear magnetic resonance characteristics shown in Table 6.

In another embodiment of the invention, Form III of Compound 1 is characterized by at least two $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by at least two $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by at least two $^{13}$C solid-state nuclear magnetic resonance peaks at chemical shifts selected from 156.6 and 132.5 ppm.

In another embodiment of the invention, Form III of Compound 1 is characterized by at least three $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by at least four $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by $^{13}$C solid-state nuclear magnetic resonance peaks at chemical shifts selected from 156.6 ppm, 156.0 ppm, 134.2 ppm, 132.5 ppm, 47.6 ppm, 46.0 ppm, 44.6 ppm, 25.5 ppm, 14.3 ppm, and 13.0 ppm.

In another embodiment of the invention, Form III of Compound 1 is characterized by at least three XRPD peaks at 2Θ angles selected from 4.8°, 9.7°, 10.3°, 13.9°, and 24.6°; or at least three $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by at least four XRPD peaks at 2Θ angles selected from 4.8°, 9.7°, 10.3°, 13.9°, and 24.6°; or at least four $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by XRPD peaks at 2Θ angles selected from 4.8°, 9.7°, 10.3°, 13.9°, and 24.6°; or at least four $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 is characterized by XRPD peaks at 2Θ angles selected from 4.8°, 9.7°, 10.3°, 13.9°, and 24.6°; or $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III of Compound 1 has the XRPD characteristics shown in Table 5 or the $^{13}$C solid-state nuclear magnetic resonance peaks shown in Table 6.

Methods of Preparation of Form I, Form II, Form III and Mixtures Thereof

The invention also relates to methods of making the solid forms of Compound 1. In general, Form I, Form II, Form III, and mixtures thereof may be obtained by dissolving Compound 1 in a suitable solvent ("the dissolution step"), preferably at a temperature above room temperature, e.g., 25° C., more preferably from about 45° C. to about 80° C. The heated solution can then be cooled ("the cooling step") to provide a solid/liquid comprising Form I, Form II, Form III or a mixture thereof, as solids. In some embodiments, the heated solutions may be filtered prior to cooling. In other embodiments, the heated solutions may be concentrated prior to or during the cooling step ("the concentration step"). In still other embodiments, the heated solutions may be treated with a cosolvent ("the cosolvent treatment step"). In some embodiments, the cosolvent (when used) can be added during the cooling step. In still other embodiments, the cooling step comprises a step-wise cooling ramp. In still other embodiments, a seed crystal or seed slurry ("the seeding step") is added during the cooling step. It is understood that any combinations of the above—may be used to obtain Form I, Form II, Form III and mixtures thereof. Once cooled, the resulting solids can be collected, washed with a suitable solvent, and dried to provide Form I, Form II, Form III, or mixtures thereof.

Methods of Making a Mixture of Form I and Form II

In one embodiment, the invention relates to a method of making a mixture of Form I and Form II of Compound 1, comprising:
 (a) heating a mixture Compound 1 in 2-propanol to 70° C. to provide a solution;
 (b) treating the solution obtained in step (a) with water while maintaining a temperature of from 50° C. to 70° C.;
 (c) cooling the aqueous mixture of step (b) to 20° C.; and
 (d) collecting the resulting solids as a mixture of Form I and Form II of Compound 1.

In one embodiment, an amorphous form of Compound 1 is used in step (a).

Methods of Making Form I

In another embodiment, the invention relates to a method of making a solid Form I of Compound 1, comprising:
 (a) heating Compound 1 and tert-butyl methyl ether (TBME) or water at 50° to provide a slurry;
 (b) cooling the slurry of step (a); and
 (c) collecting the resulting solids as Form I of Compound 1.

In one embodiment, an amorphous form of Compound 1 is used in step (a) in the embodiment immediately above.

In another embodiment, the invention relates to either of the two embodiments described immediately above, further comprising concentrating the slurry of step (b) prior to cooling the slurry.

In another embodiment, the invention relates to a method of making Form I of Compound 1, comprising:
 (a) heating Compound 1 and 2-propanol to 50-55° to provide a solution;
 (b) cooling the solution of step (a) to 25° C.;
 (c) treating the cooled solution of step (b) with water; and
 (d) collecting the resulting solids as Form I of Compound 1.

In another embodiment, the invention relates to the embodiment described immediately above, wherein an amorphous form of Compound 1 or mixture Form I and Form II of Compound 1 is used in step (a).

Methods of Making Form II

In another embodiment, the invention relates to a method of making Form II of Compound 1, comprising:
 (a) heating a mixture of Compound 1 and 2-propanol to 70° to provide a solution;
 (b) filtering the solution of step (a);
 (c) cooling the filtrate from step (b) to 55° C.;
 (d) treating the cooled solution of step (c) with water;
 (e) cooling the water-treated mixture of step (d) to 20° C.; and
 (f) collecting the resulting solids as Form II of Compound 1.

In another embodiment, the invention relates to the method described in the embodiment immediately above, further comprising seeding the water-treated solution of step (d); further mixing the seeded solution at 55° C.; and treating the seeded solution with water before cooling to 20° C.

In another embodiment, the invention relates to either of the two embodiments described immediately above, wherein an amorphous form of Compound 1 or mixture Form I and Form II of Compound 1 is used in step (a).

In another embodiment, the invention relates to a method of making Form II of Compound 1, comprising:
 (a) heating a mixture of Compound 1 (mixture of Form I and Form II), 2-propanol and water to 55-60° C. to provide a solution;
 (b) filtering the solution of step (a);
 (c) heating the filtrate of step (b) to 68-70° C.;
 (d) treating the filtrate from step (c) with water while maintaining a temperature of 68-70° C.;

(e) cooling the water-treated filtrate from step (d) to 62-66° C.;
(f) seeding the water-treated solution of step (d) with a seeding slurry comprising Form II of Compound 1, water and isopropanol to provide a seeded mixture;
(g) cooling the seeded mixture of step (f) to 55° C.
(h) mixing the seeded solution of step (e) at 55° C.;
(i) treating the seeded solution of step (h) with water to provide a mixture;
(j) mixing the mixture of step (i) at 55° C.;
(k) cooling the cooled-mixture of step (j) to 20° C.; and
(l) collecting the resulting solids as Form II of Compound 1.

In another embodiment, the invention relates to the embodiment described immediately above, wherein an amorphous form of Compound 1 or mixture Form I and Form II of Compound 1 is used in step (a).

Methods of Making Form III

In another embodiment, the invention relates to a method of making Form III of Compound 1, comprising:
(a) heating a mixture of Compound 1 (Form II) and methanol to 50-55° C. to provide a solution;
(b) concentrating the solution of step (a) at 40-45° C.;
(c) cooling the concentrated solution from step (b) to 25° C.; and
(d) collecting the resulting solids as Form III of Compound 1.

In another embodiment, the invention relates to the embodiment described immediately above, wherein Form I of Compound 1 is used in step (a).

Methods of Treatment

The compounds of the invention are selective inhibitors of glycine transporter-1 (GlyT1). The medicinal concepts discussed herein, are considered of high interest as field of application for the active compounds of the present invention. The active compounds of the present invention can be used for the development of medicaments. Such medicaments are preferably used for the treatment of diseases in which the inhibition of GlyT1 can evolve a therapeutic, prophylactic or disease modifying effect. Preferably, the medicaments may be used to treat illnesses such as psychoses, dysfunction in memory and learning, schizophrenia (positive and negative symptoms of schizophrenia and cognitive impairment associated with schizophrenia), dementia like Alzheimer's disease and other diseases in which cognitive processes are impaired, such as attention deficit disorders, Parkinson's disease, epilepsy and/or bipolar disorder.

The medicaments are for use in a method, preferably a therapeutic method, to improve perception, concentration, cognition, learning or memory, like those occurring in particular in conditions, diseases and/or syndromes such as:

mild cognitive impairment, amnestic mild cognitive impairment, age-associated learning and memory impairments, age-associated memory losses, vascular dementia, craniocerebral trauma, stroke, dementia occurring after strokes (post stroke dementia), post-traumatic dementia, general concentration impairments, concentration impairments in children with learning and memory problems, Alzheimer's disease, mild Alzheimer's disease, mild-to-moderate Alzheimer's disease, moderate-to-severe Alzheimer's disease, prodromal Alzheimer's disease, Lewy body dementia, dementia with degeneration of the frontal lobes, including Pick's syndrome, Parkinson's disease, progressive nuclear palsy, dementia with corticobasal degeneration, amyotropic lateral sclerosis (ALS), Huntington's disease, multiple sclerosis, thalamic degeneration, Creutzfeld-Jacob dementia, HIV dementia, epilepsy, temporal lobe epilepsy, Korsakoff's psychosis or cognitive impairment associated with schizophrenia, prodromal phase of schizophrenia, major depressive disorder, depression, Parkinson's disease, epilepsy, schizo-affective disorder or bipolar disorder.

Another aspect of the present invention concerns the treatment of a disease which is accessible by GlyT1-inhibition, in particular sleep disorders like insomnia or narcolepsy, bipolar disorder, depression, substance use disorders/abuse disorders, hearing disorders, attention deficit (hyperactive) disorder, inflammatory pain, neuropathic pain, autism spectrum disorders or disorders of impulse control.

The compounds of the invention can be used in or as a medicament.

Such a medicament preferably is for a therapeutic or prophylactic, preferably therapeutic method in the treatment of a CNS disease.

In an alternative use, the medicament is for the treatment of a CNS disease, the treatment of which is accessible by the inhibition of GlyT1.

In an alternative use, the medicament is for the treatment of a disease that is accessible by the inhibition of GlyT1.

In an alternative use, the medicament is for the use in a method for the treatment of Alzheimer's disease, schizophrenia (positive and negative symptoms) or cognitive impairment associated with Alzheimer's disease or associated with schizophrenia.

In a further aspect of the invention, the present invention relates to a method of treatment or prevention of a condition or disease selected from the above listed groups of conditions and diseases, wherein the method comprises the administration of a therapeutically effective amount of a compound according to the invention in a human being in need thereof.

The dose range of a compound of the present invention applicable per day is usually from 0.1 to 5000 mg, preferably from 0.1 to 1000 mg, preferably from 2 to 500 mg, more preferably from 5 to 250 mg, most preferably from 10 to 100 mg. A dosage unit (e.g. a tablet) preferably may contain between 2 and 250 mg, particularly preferably between 10 and 100 mg of the active compounds according to the invention.

Another aspect of the invention concerns the compounds of the invention for use in a therapeutic method or for use as a medicament. If indicated the therapeutic method or the medicament is preferably for the treatment of a condition or a disease selected from the group of conditions or a diseases as outlined above in this section entitled "Method of Treatment".

Another aspect of the invention concerns the compounds of the invention for use in the manufacture of a medicament for the treatment of a condition or a disease selected from the group of conditions or a diseases as outlined above in this section entitled "Method of Treatment".

Pharmaceutical Composition

Suitable preparations for administering compounds of the invention will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 0.05 to 90 wt.-%, preferably 0.1 to 50 wt.-% of the composition as a whole.

Suitable tablets may be obtained, for example, by mixing the active substance with known excipients, for example inert diluents such as calcium carbonate, calcium phosphate, lactose/lactose monohydrate, or microcrystalline cellulose; disintegrants such as maize starch, alginic acid or croscarmellose sodium; binders such as starch or gelatin; lubricants such as magnesium stearate or talc; and/or agents for delaying release, such as carboxymethyl cellulose, cellulose acetate phthalate, or polyvinyl acetate. The tablets may also comprise several layers.

The term "active substance" denotes one or more of compounds of Form I, Form II or Form III. In the case of one of the aforementioned combinations with one or more other active substances the term "active substance" may also include the additional active substances. Standard procedures should be considered for the preparation of any the herein mentioned pharmaceutical formulations.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly, the tablet coating may consist of a number or layers to achieve delayed release, possibly using the excipients mentioned above for the tablets.

For oral administration, the tablets may of course contain, apart from the abovementioned carriers, additives such as sodium citrate, calcium carbonate and dicalcium phosphate together with various additives such as starch, preferably potato starch, gelatin and the like. Moreover, lubricants such as magnesium stearate, sodium lauryl sulphate and talc may be used at the same time for the tabletting process. In the case of aqueous suspensions the active substances may be combined with various flavor enhancers or colorings in addition to the excipients mentioned above.

Active ingredients/substances or active moieties may be conveniently administered in liquid form either in a lipophilic or hydrophilic carrier system, either as a solution or a suspension, mixed with a single carrier excipient or mixed with a complex carrier medium made up of several components. Encapsulation of such liquid formulations in capsules, either soft (gelatin) or hard (gelatin-)capsules potentially offers a very convenient way of administering such pharmacologically active substances.

Syrups or elixirs containing the active substance according to the invention may additionally contain a sweetener such as saccharine, cyclamate, glycerol or sugar and a flavor enhancer, e.g. a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p hydroxybenzoates.

Capsules containing the active substance of the invention may, for example, be prepared by mixing the active substance with inert carriers such as lactose or sorbitol and packing them into gelatin capsules.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The dosage for oral administration for humans is from 0.5-1000 mg per administration with one or more administrations per day.

However, it may sometimes be necessary to depart from the amounts specified, depending on the body weight, the route of administration, the individual response to the active substance, the nature of its formulation and the time or interval over which the active substance is administered. Thus, in some cases it may be sufficient to use less than the minimum dose given above, whereas in other cases the upper limit may have to be exceeded. When administering large amounts it may be advisable to divide them up into a number of smaller doses spread over the day.

In one embodiment, the invention relates to a pharmaceutical composition comprising Form I, Form II, Form III, or a mixture of at least two of Form I, Form II, and Form III, and a pharmaceutically acceptable excipient.

In another embodiment, the invention relates to a pharmaceutical composition comprising Form I of Compound 1 and a pharmaceutically acceptable excipient.

In another embodiment, the invention relates to a pharmaceutical composition comprising Form II of Compound 1 and a pharmaceutically acceptable excipient.

In another embodiment, the invention relates to a pharmaceutical composition comprising Form III of Compound 1 and a pharmaceutically acceptable excipient.

In another embodiment, the invention relates to a pharmaceutical composition comprising at least two of Form I, Form II, and Form III of Compound 1 and a pharmaceutically acceptable excipient.

The following further examples of pharmaceutical dosage forms illustrate the present invention without restricting its scope.

| Hard gelatin capsules | | Suppository Composition | |
|---|---|---|---|
| active substance | 150.0 mg | active substance | 150.0 mg |
| lactose | 87.0 mg | polyethyleneglycol 1500 | 550.0 mg |
| corn starch (dried) | 80.0 mg | polyethyleneglycol 6000 | 460.0 mg |
| magnesium stearate | 3.0 mg | polyoxyethylene sorbitan monostearate | 840.0 mg |
| | 320.0 mg | | |
| | | | 2000.0 mg |

| Tablets | | | |
|---|---|---|---|
| active substance | 100.0 mg | | 150.0 mg |
| lactose | 80.0 mg | | 89.0 mg |
| corn starch | 34.0 mg | | 40.0 mg |
| polyvinylpyrrolidone | 4.0 mg | | 10.0 mg |
| magnesium stearate | 2.0 mg | | 1.0 mg |
| | 220.0 mg | | 290.0 mg |

Combination Therapy/Combination with Other Active Substances

The above polymorphs Form I, Form II or Form III can also be administered together with another active compound. The invention also refers to a pharmaceutical formulation that provides such a combination of active ingredients, wherein one is an inventive solid form of the Compound 1.

Such combinations may be fixed dose combinations (the active ingredients that are to be combined are subject of the same pharmaceutical formulation) or free dose combinations (active ingredients are in separate pharmaceutical formulations).

Consequently, a further aspect of the present invention is a combination of a compound of the invention, with another active compound for example selected from the group of antipsychotics such as haloperidol, clozapine, risperidone, quetiapine, aripripazole, asenapine and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aß (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists or positive allosteric modulators; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The compounds of the invention may also be used in combination with immunotherapies such as e.g. active immunization with Abeta or parts thereof or passive immunization with humanized anti-Abeta antibodies or antibody fragments for the treatment of the above-mentioned diseases and conditions.

The compounds of the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, and lurasidone.

The compounds of the invention also may be combined with antidepressants like amitriptyline imipramine hydrochloride (TOFRANIL), imipramine maleate (SURMONTIL), lofepramine, desipramine (NORPRAMIN), doxepin (SINEQUAN, ZONALON), trimipramine (SURMONTIL).

Or the compounds of the invention also may be combined with serotonin (5-HT) reuptake inhibitors such as alaproclate, citalopram (CELEXA, CIPRAMIL) escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensme and tesofensine.

The combinations according to the present invention may be provided in one and the same dosage form, i.e. in form of a combination preparation, for example the two components may be incorporated in one tablet, e. g., in different layers of said tablet.

The dosage or administration forms are not limited; in the frame of the present invention, any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently ⅕ of the normally recommended lowest dose up to 1/1 of the normally recommended dose.

The dosage forms are administered to the patient, for example, 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

EXAMPLES

Example 1

Preparation of Amorphous Compound 1: The amorphous form of Compound 1 ("amorphous Compound 1") is prepared as described in Example 50 of WO2013017657. Chiral separation of a diastereomeric mixture (prepared according to Example 49 of WO2013017657) is performed as described in Example 49 except the flow rate is 12 ml/min instead of 15 ml/min. Solvents are removed from the resulting eluent under reduced pressure to provide amorphous Compound 1 as a solid. A typical XRPD pattern obtained of a sample of the amorphous Compound 1 is shown in FIG. 1.

Example 2

Preparation of a mixture of Form I and Form II of Compound 1: A reactor is charged with the amorphous form of Compound 1 (20 g) and 2-propanol (75 mL) and the contents are heated to 70° C. The resulting solution is treated with water (111 mL) while maintaining a batch temperature of not less than 50° C. The reactor contents are then cooled to 20° C. over 1.5 hr. The solids are collected by filtration, rinsed with water, and dried under reduced pressure at 40° C. to provide a mixture of Form I and Form II of Compound 1 (15.4 g, 77% yield) based on the characterization methods described herein and having a molar ratio of 61:39 (Form I:Form II) determined by Raman spectroscopy.

Example 3A

Preparation of Form I of Compound 1: Amorphous Compound 1 (50 mg) is treated with 4 ml of tert-butyl methyl ether (TBME) and the resulting slurry is stirred for 2 h at 50° C. About 2 ml of solvent is removed under reduced pressure. The mixture is then filtered and the solids dried overnight in a vacuum oven at 40° C. to provide Form I of Compound 1.

Form I of Compound 1 can also be prepared according to the procedure described immediately above using water instead of TBME.

Example 3B

Preparation of Form I of Compound 1: A mixture of Form I and Form II of Compound 1 (14 g, 0.029 mol) is dissolved in 2-propanol (140 mL) and heated to 50-55° C. The resulting solution is allowed to cool to room temperature then treated with water (500 mL) while being rigorously mixed. The agitation is then stopped and the reactor contents are allowed to stand without agitation for at least 30 min. The resulting solids are then collected by filtration, washed with water and then heptane and air-dried for 2 hours to provide 14.6 g of Form I of Compound 1.

Example 4A

Preparation of Form II of Compound 1: A reactor is charged with a mixture of Form I and Form II of Compound 1 (37 g, 0.072 mol) and 140 ml of isopropanol, and the reactor contents are heated to about 70° C. The resulting solution is vacuum filtered (Buchner funnel equipped with filter paper) and the filtrate cooled to about 55° C. The solution is then treated with water (111 mL) and seeded with 0.74 g of Form I of Compound 1 while being rigorously mixed at 55° C. for at least 4 hours. Additional water (95.14 g) is added to the stirred mixture over at least 6 hours, the agitation is stopped, and the reactor contents are cooled to 20° C. over at least 4 hours. The resulting solids are then collected by filtration, washed with water and then heptane and air-dried to provide Form II of Compound 1.

A similar result is obtained if the seeding is done with Form II, or a mixture for Form I and Form II.

Example 4B

Preparation of Form II of Compound 1: A reactor is charged with a mixture of Form I and Form II of Compound 1 (100 g, 0.195 mol), isopropanol (500 ml) and water (100 ml). The reactor contents are heated with stirring to 55-60° C. and the resulting solution is vacuum filtered (Buchner funnel equipped with filter paper) at 55-60° C. The stirred filtrate is heated to 68-70° C., treated with 600 mL of water while maintaining the temperature at 68-70° C., and cooled to 62-66° C. over 30 min. The solution is seeded with a seed slurry of Form II of Compound 1 (2 g) in mixture of 20 g of water and 4 g of isopropyl alcohol aged at 62-66° C. for 0.5 h, and cooled to 55° C. over 2-3 hrs. The resulting mixture is stirred at 55° C. for 2 hours, cooled to 20° C. over 4-6 hours, and filtered. The solids are washed with water (200 mL) and dried at 50-70° C. for at least 8 hours to provide Form II of Compound 1.

Example 5

Preparation of Form III of Compound 1: A reactor is charged with Form II of Compound 1 (20 g, 39 mmol) and methanol (200 mL), and the reactor contents are heated to 50-55° C. The reactor contents are then concentrated under reduced pressure and at 40-45° C. to approximately 80 ml, cooled to room temperature over at least 1 hour, and stirred for an additional 2 hours at room temperature. The solids are collected by filtration, washed with heptane, and dried under reduced pressure at 50° C. for 10 hours to provide 19.46 g of Form III of Compound 1.

What is claimed is:

1. A solid Form II of Compound 1 having the structural formula:

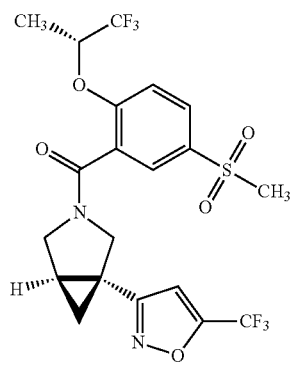

wherein the Form II has characteristic X-ray reflections at the following d values:
4.1°, 4.6°, 10.0°, 16.7°, and 18.0° (2-theta); or
characteristic $^{13}$C solid-state NMR chemical shifts selected from:
130.1 ppm, 46.6 ppm, and 25.0 ppm; or
at least three characteristic $^{19}$F solid-state nuclear magnetic resonance peaks at chemical shifts selected from −64.0, −65.6, −66.6, −78.2, and −79.1 ppm.

2. The solid Form II of Compound 1 according to claim 1, characterized by XRPD peaks at 2Θ angles selected from 4.1°, 4.6°, 10.0°, 16.7°, and 18.0°.

3. The solid Form I of Compound 1 according to claim 1, characterized by $^{19}$F solid-state nuclear magnetic resonance peaks at chemical shifts selected from −64.0, −65.6, −66.6, −78.2, and −79.1 ppm.

4. A pharmaceutical composition comprising the solid form of the compound according to claim 1, optionally together with one or more inert carriers and/or diluents.

* * * * *

UNITED STATES PATENT AND TRADEMARK OFFICE
CERTIFICATE OF CORRECTION

PATENT NO. : 11,447,474 B2
APPLICATION NO. : 16/862608
DATED : September 20, 2022
INVENTOR(S) : Joe Ju Gao et al.

It is certified that error appears in the above-identified patent and that said Letters Patent is hereby corrected as shown below:

In the Claims

At Column 24, Lines 39-40:
The text "has characteristic X-ray reflections at the following d values"
Should read:
-- has characteristic X-ray powder diffraction (XRPD) peaks at 2Θ angles selected from --

At Column 24, Line 41:
The term "(2-theta)" should be deleted

At Column 24, Line 51:
The term "Form I"
Should read:
-- Form II --

Signed and Sealed this
Fourteenth Day of November, 2023

Katherine Kelly Vidal
*Director of the United States Patent and Trademark Office*